US006969715B2

(12) United States Patent
South et al.

(10) Patent No.: US 6,969,715 B2
(45) Date of Patent: Nov. 29, 2005

(54) 6-MEMBERED HETEROCYCLIC COMPOUNDS USEFUL FOR SELECTIVE INHIBITION OF THE COAGULATION CASCADE

(75) Inventors: Michael S. South, St. Louis, MO (US); Ronald K. Webber, St. Charles, MO (US); Horng-Chih Huang, Chesterfield, MO (US); Mihaly V. Toth, St. Louis, MO (US); Alan E. Moormann, Weldon Spring, MO (US); Jeffery S. Snyder, Manchester, MO (US); Jeffrey A. Scholten, Chesterfield, MO (US); Danny J. Garland, Ballwin, MO (US); Melvin L. Rueppel, St. Louis, MO (US); William L. Neumann, St. Louis, MO (US); Scott Long, Ballwin, MO (US); Wei Huang, Wildwood, MO (US); John Trujillo, St. Peters, MO (US); John J. Parlow, Arnold, MO (US); Darin E. Jones, Ballwin, MO (US); Brenda Case, St. Louis, MO (US); Michael J. Hayes, St. Louis, MO (US)

(73) Assignee: Pharmacia Corporation, St. Louis, MO (US)

( * ) Notice: Subject to any disclaimer, the term of this patent is extended or adjusted under 35 U.S.C. 154(b) by 122 days.

(21) Appl. No.: 10/263,637

(22) Filed: Oct. 3, 2002

(65) Prior Publication Data

US 2003/0139405 A1 Jul. 24, 2003

Related U.S. Application Data

(60) Provisional application No. 60/332,107, filed on Nov. 21, 2001, provisional application No. 60/331,891, filed on Nov. 21, 2001, provisional application No. 60/350,052, filed on Nov. 7, 2001, provisional application No. 60/332,857, filed on Nov. 6, 2001, provisional application No. 60/338,623, filed on Oct. 24, 2001, and provisional application No. 60/326,721, filed on Oct. 3, 2001.

(51) Int. Cl.[7] ............... C07D 253/06; A61K 31/53; A61P 9/10
(52) U.S. Cl. ............................ 514/242; 544/182
(58) Field of Search ................. 544/182; 514/242

(56) References Cited

U.S. PATENT DOCUMENTS

| 4,489,096 A | 12/1984 | Terao et al. |
|---|---|---|
| 4,851,413 A | 7/1989 | Terao et al. |
| 4,992,469 A | 2/1991 | Ozawa et al. |
| 5,304,658 A | 4/1994 | Terao et al. |
| 5,441,960 A | 8/1995 | Bernstein et al. |
| 5,656,645 A | 8/1997 | Tamura et al. |
| 5,658,930 A | 8/1997 | Tamura et al. |
| 5,668,289 A | 9/1997 | Sanderson et al. |
| 5,741,819 A | 4/1998 | Illig et al. |
| 5,792,779 A | 8/1998 | Sanderson et al. |
| 5,861,380 A | 1/1999 | Gyorkos et al. |
| 5,866,573 A | 2/1999 | Sanderson et al. |
| 5,869,487 A | 2/1999 | Coburn et al. |
| 5,872,138 A | 2/1999 | Naylor-Olsen et al. |
| 6,008,351 A | 12/1999 | Tamura et al. |
| 6,011,158 A | 1/2000 | Tamura et al. |
| 6,037,356 A | 3/2000 | Lu et al. |
| 6,180,627 B1 | 1/2001 | Blagg et al. |

FOREIGN PATENT DOCUMENTS

| DE | 198 51 421 A1 | 5/2000 |
|---|---|---|
| EP | 0 354 495 A1 | 2/1990 |
| EP | 0 528 633 B1 | 2/1993 |
| EP | 0 826 671 A1 | 3/1998 |
| EP | 0 936 216 A | 8/1999 |
| EP | 0 940 400 A1 | 9/1999 |
| EP | 0 997 474 A1 | 5/2000 |
| WO | WO 93/21214 A1 | 10/1993 |
| WO | WO 96/18644 A1 | 6/1996 |
| WO | WO 96/33974 A1 | 10/1996 |
| WO | WO 96/39380 A1 | 12/1996 |
| WO | WO 96/40100 A1 | 12/1996 |
| WO | WO 97/01338 A1 | 1/1997 |
| WO | WO 97/30708 A1 | 8/1997 |
| WO | WO 97/40024 A1 | 10/1997 |
| WO | WO 97/46207 A2 | 12/1997 |
| WO | WO 98/08840 A1 | 3/1998 |
| WO | WO 98/09949 A1 | 3/1998 |
| WO | WO 98/09987 A1 | 3/1998 |
| WO | WO 98/10763 A1 | 3/1998 |
| WO | WO 98/16525 A1 | 4/1998 |
| WO | WO 98/16547 A1 | 4/1998 |
| WO | WO 98/17274 A1 | 4/1998 |
| WO | WO 98/31670 A1 | 7/1998 |
| WO | WO 98/42342 A1 | 10/1998 |
| WO | WO 98/47876 A1 | 10/1998 |
| WO | WO 98/50420 A1 | 11/1998 |
| WO | WO 99/00121 A1 | 1/1999 |
| WO | WO 99/00126 A1 | 1/1999 |
| WO | WO 99/00128 A1 | 1/1999 |
| WO | WO 99/11267 A1 | 3/1999 |
| WO | WO 99/26920 A1 | 6/1999 |

(Continued)

OTHER PUBLICATIONS

International Search Report from PCT/US02/31769 dated Dec. 19, 2002.

(Continued)

*Primary Examiner*—Venkataraman Balasubramanian

(57) ABSTRACT

The present invention relates to compounds, and prodrugs thereof, compositions and methods useful for preventing and treating thrombotic conditions in mammals. The compounds of the present invention, and prodrugs thereof, selectively inhibit certain proteases of the coagulation cascade.

14 Claims, No Drawings

FOREIGN PATENT DOCUMENTS

| | | |
|---|---|---|
| WO | WO 99/26926 A1 | 6/1999 |
| WO | WO 99/36426 A1 | 7/1999 |
| WO | WO 99/43660 A1 | 9/1999 |
| WO | WO 99/48892 A1 | 9/1999 |
| WO | WO 99/59591 A1 | 11/1999 |
| WO | WO 99/61442 A1 | 12/1999 |
| WO | WO 99/62538 A1 | 12/1999 |
| WO | WO 99/64446 A1 | 12/1999 |
| WO | WO 00/18762 A1 | 4/2000 |
| WO | WO 00/26210 A1 | 5/2000 |
| WO | WO 00/26211 A1 | 5/2000 |
| WO | WO 00/32574 A1 | 6/2000 |
| WO | WO 00/39102 A1 | 7/2000 |
| WO | WO 00/69826 A1 | 11/2000 |
| WO | WO 00/69832 A1 | 11/2000 |
| WO | WO 00/69833 A1 | 11/2000 |
| WO | WO 01/68605 A1 | 9/2001 |
| WO | WO 01/77079 A2 | 10/2001 |
| WO | WO 01/77097 A1 | 10/2001 |
| WO | WO 01/79155 A2 | 10/2001 |
| WO | WO 01/87842 A1 | 11/2001 |
| WO | WO 01/87851 A1 | 11/2001 |
| WO | WO 01/87854 A1 | 11/2001 |
| WO | WO 02/42272 A2 | 5/2002 |

OTHER PUBLICATIONS

Coburn, C.A., "Small–molecule direct thrombine inhibitors 1997–2000." Expert Opinions on Therapeutic Patents, 2001, 721–738, vol. 11, No. 5.

XP–002182132—Darvas, et al., "Investigation of the Common Mechanism of Action of Antibacterial Compounds Containing ,gamma,–pyridone–.beta.–carboxylic acid Structure by Principal Component." Arzneim.–Forshc., 1979, pp. 1334–1339, vol. 29, 9.

Handin, R., "Bleeding and Thrombosis." Harrison's Principles of Internal Medicine, 12th Edition, 1991, pp. 348–353, McGraw–Hill, Inc., New York.

XP–002172033—Kohama et al., "Preparation of Piperidinyloxyacetylaminobenzoylalanine Derivatives and Analogs as Antithrombotics," JP 07,233,148.

Majerus, et al. "Anticoagulant, Thrombolytic, and Antiplatlet Drugs." Goodman & Gilman's The Pharmacological Basis of Therapeutics, Ninth Edition, 1996, pp. 1341–1359, McGraw–Hill, New York.

XP–002187583—Moerner, Hoppe–Seyler's Z. Physiol. Chem., 69, 1910;357.

Patel et al., "Directed Aminomethylation of 3–Hydroxy–3(1H)–pyridinones and 3–hydroxy–4(1H)–pyridinones: Synthesis of iso–Deferiprone." Tetrahedron, 1996, pp. 1835–1840, vol. 52, No. 5.

Rauch et al., "Thrombus Formation on Atheroscleratic Plaques: Pathogenesis and Clinical Consequences." Animals of Internal Medicine, 2001, pp. 224–233, vol. 134, No. 3.

Sanderson et al., "L–373,890, An Achiral, Noncovalent, Subnamomolar Thrombin Inhibitor." Bioorganic & Medicinal Chemistry Letters, vol. 7, No. 12, pp. 1497–1500, 1997.

XP–002182410—Trecourt et al., "First Synthesis of (+–)–harzianopyridone by Metalation of Polysubstituted O–pyridylcarbamates." J. Heterocycl. Chem., 1995, pp. 1117–1114, vol. 32, No. 4.

Tulinsky et al., "Novel Asymmetric Synthesis of Atropisomeric 6–Aryl Pyrazinones via an unusual Chirally Transfer Process." J. Org. Chem., 1999, pp. 93–100, vol. 64, No. 1.

Van Aken, et al., "Anticoagulation: The Present and Future." Clin. Appl. Thromiosis/Hemostasis, 2001, vol. 7, No. 3.

6-MEMBERED HETEROCYCLIC COMPOUNDS USEFUL FOR SELECTIVE INHIBITION OF THE COAGULATION CASCADE

CROSS REFERENCE TO RELATED APPLICATIONS

This application claims priority from Provisional Application Ser. No. 60/326,721 filed Oct. 3, 2001, No. 60/338,623 filed Oct. 24, 2001, No. 60/332,857 filed Nov. 6, 2001, No. 60/350,052 filed on Nov. 7, 2001, and No. 60/332,107 and 60/331,891 both filed on Nov. 21, 2001, which are all hereby incorporated by reference in their entirety.

FIELD OF THE INVENTION

The present invention relates to compounds, compositions and methods for preventing and treating thrombotic conditions such as coronary artery and cerebrovascular disease. More particularly, the invention relates to compounds, and prodrugs thereof, that selectively inhibit serine proteases of the coagulation cascade.

BACKGROUND OF THE INVENTION

Hemorrhage, intravascular thrombosis, and embolism are common clinical manifestations of many diseases (see R. I. Handin in *Harrison's Principles of Internal Medicine* (J. D. Wilson, et al. eds., 12th ed. 1991) New York, McGraw-Hill Book Co., pp. 348–351). The normal hemostatic system limits blood loss by precisely regulated interactions between components of the vessel wall, circulating blood platelets, and plasma proteins. Unregulated activation of the hemostatic system, however, may cause thrombosis, which can reduce blood flow to critical organs like the brain and myocardium.

Physiological systems control the fluidity of blood in mammals (see P. W. Majerus, et al. in *Goodman & Gilman's The Pharmacological Basis of Therapeutics* (J. G. Hardman & L. E. Limbird, eds., 9th ed. 1996) New York, McGraw-Hill Book Co., pp. 1341–1343). Blood must remain fluid within the vascular systems and yet quickly be able to undergo hemostasis. Hemostasis, or clotting, begins when platelets first adhere to macromolecules in subendothelian regions of injured and/or damaged blood vessels. These platelets aggregate to form the primary hemostatic plug and stimulate local activation of plasma coagulation factors leading to generation of a fibrin clot that reinforces the aggregated platelets. Plasma coagulation factors, also referred to as protease zymogens, include factors II, V, VII, VIII, IX, X, XI, and XII. These coagulation factors or protease zymogens are activated by serine proteases leading to coagulation in a so called "coagulation cascade" or chain reaction.

Coagulation or clotting occurs in two ways through different pathways. An intrinsic or contact pathway leads from XII to XIIa to XIa to IXa and to the conversion of X to Xa. Factor Xa in combination with factor Va converts prothrombin (II) to thrombin (IIa) leading to conversion of fibrinogen to fibrin. Polymerization of fibrin leads to a fibrin clot. An extrinsic pathway is initiated by the conversion of coagulation factor VII to VIIa by factor Xa. Factor VIIa, a plasma protease, is exposed to, and combines with its essential cofactor tissue factor (TF) which resides constitutively beneath the endothelium. The resulting factor VIIa/TF complex proteolytically activates its substrates, factors IX and X, triggering a cascade of reactions that leads to the generation of thrombin and a fibrin clot as described above.

While clotting as a result of an injury to a blood vessel is a critical physiological process for mammals, clotting can also lead to disease states. A pathological process called thrombosis results when platelet aggregation and/or a fibrin clot blocks (i.e., occludes) a blood vessel. Arterial thrombosis may result in ischemic necrosis of the tissue supplied by the artery. When the thrombosis occurs in a coronary artery, a myocardial infarction or heart attack can result. A thrombosis occurring in a vein may cause tissues drained by the vein to become edematous and inflamed. Thrombosis of a deep vein may be complicated by a pulmonary embolism. Preventing or treating clots in a blood vessel may be therapeutically useful by inhibiting formation of blood platelet aggregates, inhibiting formation of fibrin, inhibiting thrombus formation, inhibiting embolus formation, and for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels.

In order to treat such conditions, researchers have sought to discover chemical compounds that efficaciously and selectively control the clotting process. In addition, such compounds may provide a better understanding of the pathways involved in the coagulation process.

Thus far, many of the compounds that have been discovered possess a polar or basic functional group which is integrally responsible for the desired biological activity. Frequently, this polar functional group is a nitrogen atom of, for example, a guanidine, alkyl-amidine or aryl-amidine group. Because these functionalities are highly basic, they remain protonated at physiologically relevant pH's. The ionic nature of such protonated species hinders their permeability across lipophilic membranes, which can reduce bioavailability when the pharmaceutical agent is administered orally.

In order to circumvent such a problem, it is often advantageous to perform a derivatization or chemical modification of the polar functionality such that the pharmaceutical agent becomes neutrally charged and more lipophilic, thereby facilitating absorption of the drug. However, for the derivatization to be useful, the derivatization must be bioconvertable at the target site or sites of desired pharmacological activity and cleaved under normal physiological conditions to yield the biologically active drug. The term "prodrug" has been used to denote such a chemically modified intermediate.

SUMMARY OF THE INVENTION

Among the various aspects of the present invention, therefore, is the provision of compounds useful for selective inhibition of certain enzymes that act upon the coagulation cascade thereby preventing and treating thrombotic conditions in mammals.

Another aspect of the present invention is the provision of prodrug compounds useful for selective inhibition of certain enzymes that act upon the coagulation cascade thereby preventing and treating thrombotic conditions in mammals. In general, these prodrug compounds undergo hydrolysis, oxidation, reduction or elimination at a derivatized amidine group to yield the active compound.

Briefly, therefore, the present invention is directed to a compound, per se, to the prodrug of the compound, to pharmaceutical compositions comprising the compound or prodrug and a pharmaceutically acceptable carrier, and to methods of use. The compound corresponds to formula (1):

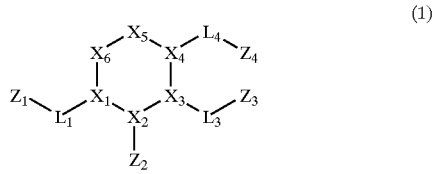

(1)

wherein:

$X_1$, $X_2$, $X_3$, $X_4$, $X_5$, and $X_6$ are each ring atoms defining a 6-membered heterocyclic ring;

$X_1$, $X_3$, and $X_4$ are independently carbon or nitrogen;

$X_2$, $X_5$, and $X_6$ are independently carbon, nitrogen, oxygen or sulfur, where $X_5$ and $X_6$ are optionally substituted with a halogen, provided no more than 4 of $X_1$, $X_2$, $X_3$, $X_4$, $X_5$, and $X_6$ are sp$^2$ hybridized;

$L_1$, $L_3$ and $L_4$ are linkages through which $Z_1$, $Z_3$, and $Z_4$, respectively, are covalently bonded to different ring atoms of the 6-membered heterocyclic ring defined by $X_1$, $X_2$, $X_3$, $X_4$, $X_5$, and $X_6$, wherein $Z_1$ is covalently bonded to $X_1$, $Z_3$ is covalently bonded to $X_3$, and $Z_4$ is covalently bonded to $X_4$, each of $L_1$, $L_3$ and $L_4$ independently being a covalent bond or comprising one or more atoms through which $Z_1$, $Z_3$, and $Z_4$ are covalently bonded to $X_1$, $X_3$ and $X_4$, respectively;

$Z_1$ is hydrocarbyl or substituted hydrocarbyl;

$Z_2$ is hydrogen, an electron pair, or a hydrogen bond acceptor covalently or datively bonded to $X_2$;

$Z_3$ comprises a 5- or 6-membered heterocyclic or aromatic ring substituted with an amidine or a derivatized amidine group, the ring atoms of the 5- or 6-membered heterocyclic or aromatic ring of $Z_3$ being carbon, sulfur, nitrogen, or oxygen wherein the 5- or 6-membered ring is optionally substituted at any position with halogen, hydroxy, haloalkyl, alkyl, carboxy, alkoxycarbonyl, or hydrocarbyloxy; and $Z_4$ comprises a 5- or 6-membered heterocyclic or carbocyclic ring, the ring atoms of the 5- or 6-membered heterocyclic or carbocyclic ring of $Z_4$ being carbon, nitrogen, oxygen, or sulfur.

Other aspects and features of this invention will be in part apparent and in part pointed out hereafter.

Abbreviations and Definitions

The term "elimination" as used herein is generally meant to encompass any one or more of the following reactions: (1) a reaction that results in a compound fragmenting into two or more compounds; and (2) a reaction that results in one or more groups being removed from a compound without being replaced by other groups.

The term "oxidation" as used herein is generally meant to encompass any one or more of the following reactions: (1) a reaction that results in an increase in the oxidation number of an atom in a compound, whether the atom is uncharged or charged and whether free or covalently bound; (2) a reaction that results in the loss of hydrogen from a compound; (3) a reaction that results in the loss or removal of one or more electrons from a compound, with or without concomitant loss or removal of a proton or protons; (4) the action or process of reacting a compound with oxygen; and (5) a reaction that results in the addition of one or more oxygen atoms to a compound.

The term "reduction" as used herein is generally meant to encompass any one or more of the following reactions: (1) any reaction which results in a decrease in the oxidation number of an atom in a compound; and (2) any reaction that results in oxygen being withdrawn from, hydrogen being added to, or an electron being added to (with or without the addition of a proton) a compound.

The term "hydrolysis" as used herein is generally meant to encompass any one or more of the following reactions: (1) any reaction which results in the addition of a nucleophile to a compound to form a new bond with concurrent loss of a group from the compound; (2) any reaction which results in the addition of water to a compound; and (3) any reaction that results in the rupture of one or more chemical bonds by reaction with, and involving the addition of, the elements of water.

The term "physiological conditions" are those conditions characteristic to an organism's (to a human beings) healthy or normal functioning.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorus, boron, sulfur, or a halogen atom. Exemplary substituted hydrocarbyl moieties include, heterocyclo, alkoxyalkyl, alkenyloxyalkyl, alkynyloxyalkyl, aryloxyalkyl, hydroxyalkyl, protected hydroxyalkyl, keto, acyl, nitroalkyl, aminoalkyl, cyano, alkylalkylthio, arylalkylthio, ketals, acetals, amides, acids, esters and the like.

The term "heteroatom" shall mean atoms other than carbon and hydrogen.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, cyclopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclos include heteroaromatics such as furanyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "acetamidyl" as used herein describes a chemical moiety represented by the formula $NR_1C(O)R_2$.

The term "carboxamido" as used herein, describes a chemical moiety represented by the formula $C(O)NR_1R_2$.

The term "alkoxycarbonyl" as used herein describes a chemical moiety represented by the formula $C(O)OR$.

The term "sulfonamido" as used herein describes a chemical moiety represented by the formula $SO_2NR_1R_2$.

The term "alkylsulfonyl" as used herein describes a chemical moiety represented by the formula $SO_2R$.

The term "sulfonamidy" as used herein describes a chemical moiety represented by the formula $NRSO_2R$.

As described herein for the terms "acetamidyl", "carboxamido", "alkocycarbonyl", "sulfonamido", "alkylsulfonyl", and "sulfonamidyl", R, $R_1$ and $R_2$ are independently hydrogen, alkyl, aryl, and arylakyl, optionally substituted with halogen, hydroxy or alkoxy.

DESCRIPTION OF THE PREFERRED EMBODIMENT

In one embodiment of the present invention, the compounds correspond to formula (1):

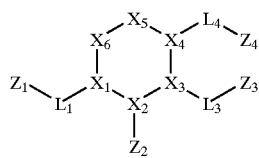

(1)

wherein:
$X_1$, $X_2$, $X_3$, $X_4$, $X_5$, and $X_6$ are each ring atoms defining a 6-membered heterocyclic ring;
$X_1$, $X_3$, and $X_4$ are independently carbon or nitrogen;
$X_2$, $X_5$, and $X_6$ are independently carbon, nitrogen, oxygen or sulfur where $X_5$ and $X_6$ are optionally substituted with a halogen, provided no more than 4 of $X_1$, $X_2$, $X_3$, $X_4$, $X_5$, and $X_6$ are $sp^2$ hybridized;

$L_1$, $L_3$ and $L_4$ are linkages through which $Z_1$, $Z_3$, and $Z_4$, respectively, are covalently bonded to different ring atoms of the 6-membered heterocyclic ring defined by $X_1$, $X_2$, $X_3$, $X_4$, $X_5$, and $X_6$, wherein $Z_1$ is covalently bonded to $X_1$, $Z_3$ is covalently bonded to $X_3$, and $Z_4$ is covalently bonded to $X_4$, each of $L_1$, $L_3$ and $L_4$ independently being a covalent bond or comprising one or more atoms through which $Z_1$, $Z_3$, and $Z_4$ are covalently bonded to $X_1$, $X_3$ and $X_4$, respectively;

$Z_1$ is hydrocarbyl or substituted hydrocarbyl;

$Z_2$ is hydrogen, an electron pair, or a hydrogen bond acceptor covalently or datively bonded to $X_2$;

$Z_3$ comprises a 5- or 6-membered heterocyclic or aromatic ring substituted with an amidine or a derivatized amidine group, the ring atoms of the 5- or 6-membered heterocyclic or aromatic ring of $Z_3$ being carbon, sulfur, nitrogen, or oxygen wherein the 5- or 6-membered ring is optionally substituted at any position with halogen, hydroxy, haloalkyl, alkyl, carboxy, alkoxycarbonyl, or hydrocarbyloxy; and $Z_4$ comprises a 5- or 6-membered heterocyclic or carbocyclic ring, the ring atoms of the 5- or 6-membered heterocyclic or carbocyclic ring of $Z_4$ being carbon, nitrogen, oxygen, or sulfur.

One aspect of the invention encompasses compounds corresponding to formula (1) wherein $X_1$, $X_3$, and $X_4$ are independently carbon or nitrogen and $X_2$, $X_5$, and $X_6$ are independently carbon, nitrogen, oxygen or sulfur. Typically, in this embodiment, no more than 4 of $X_1$, $X_2$, $X_3$, $X_4$, $X_5$, and $X_6$ are $sp^2$ hybridized. In one alternative of this embodiment, $X_1$, $X_2$, $X_3$, $X_4$, $X_5$, and $X_6$ are independently carbon or nitrogen, provided at least one of $X_1$, $X_2$, $X_3$, $X_4$, $X_5$, and $X_6$ is nitrogen. In another alternative of this embodiment, $X_3$ is nitrogen, $X_2$ is carbon, and $Z_2$ is hydrogen, fluorine, oxygen, or sulfur. In yet another alternative of this embodiment, $X_2$ is nitrogen, oxygen or sulfur and $Z_2$ is hydrogen, an electron pair, or a hydrogen bond acceptor. In yet another alternative of this embodiment, $X_2$ is nitrogen and $Z_2$ is hydrogen, oxygen, amino, or acyl. In still another alternative of this embodiment, $X_2$ is carbon and $X_3$ is nitrogen. Still another alternative of this embodiment embraces compounds where at least one of $X_1$, $X_2$, $X_3$, $X_4$, $X_5$, and $X_6$ is carbon and the carbon is $sp^3$ hybridized. For each of the alternatives of this embodiment, $X_5$ may be optionally substituted with a halogen. A preferred halogen is chlorine. A more preferred halogen is fluorine.

In another aspect of compounds corresponding to formula (1), $X_1$, $X_2$, $X_3$, $X_4$, $X_5$, $X_6$, and $Z_2$ are as defined for compounds having formula (1) above and are selected to form the following 6-membered heterocyclic rings: piperidinone, dihydropyrimidinone, tetrahydropyrimidinone, dehydropiperidinedione, dihydropyridazinone, dihydroisoxazinone, tetrahydrotriazinedione, tetrahydrotriazinone, piperidine, and piperazine. In one alternative of this embodiment, $X_1$, $X_2$, $X_3$, $X_4$, $X_5$, $X_6$, and $Z_2$ are selected to form a heterocyclic ring selected from tetrahydrotriazinone, piperidinone, dihydropyrimidinone, tetrahydropyrimidinone, piperidine, and piperazine. In another alternative of this embodiment, $X_1$, $X_2$, $X_3$, $X_4$, $X_5$, $X_6$, and $Z_2$ are selected to form a heterocyclic ring selected from tetrahydrotriazinone, piperidinone, dihydropyrimidinone, and tetrahydropyrimidinone. In a preferred alternative of this embodiment, the heterocyclic ring defined by $X_1$, $X_2$, $X_3$, $X_4$, $X_5$, $X_6$, and $Z_2$ is tetrahydrotriazinone.

In one embodiment of compounds having formula (1), $L_1$ is $X_9NH$ wherein $X_9$ is covalently bonded to $Z_1$ and $X_9$ is a bond or $(CH_2)_m$ wherein m is 1 to 5. In one alternative of this embodiment (i.e., when $L_1$ is $X_9NH$), m is 1 to 2. In another alternative of this embodiment, $L_1$ is $X_9NH$ wherein $X_9$ is covalently bonded to $Z_1$ and is a bond. In yet another alternative of this embodiment, $L_1$ is a methylene or ethylene group. In another alternative of this embodiment, $L_1$ optionally contains a bond to $X_6$ to form a fused ring with the heterocyclic ring.

In one embodiment of compounds corresponding to formula (1), $L_3$ is selected from the group consisting of a glycine derivative, an alanine derivative, an amino derivative, and a sulfonyl derivative. In one alternative of this embodiment, $L_3$ is a glycine derivative. In another alternative of this embodiment, $L_3$ is $CH_2CONHCH_2$ where $Z_3$ is bonded to the methylene bonded to the amine group.

In one embodiment of compounds corresponding to formula (1), $L_4$ is selected from the group consisting of a bond, methylene, ethylene, or an optionally substituted heteroatom selected from nitrogen, oxygen, sulfur and phosphorus. In one alternative of this embodiment, $L_4$ is $(CH_2)_m$ wherein m is 0 to 2. In a preferred alternative of this embodiment, $L_4$ is a bond.

In one embodiment of compounds corresponding to formula (1), $Z_1$ is hydrocarbyl or substituted hydrocarbyl. In one alternative of this embodiment (i.e., when $Z_1$ is hydrocarbyl or substituted hydrocarbyl), $Z_1$ is optionally substituted $C_2$ to $C_8$ alkyl, optionally substituted $C_3$ to $C_6$ cycloalkyl and optionally substituted phenyl. In another alternative of this embodiment, $Z_1$ is selected from the group consisting of optionally substituted cyclopropyl, isopropyl, cyclobutyl, isobutyl, sec-butyl, methyl, ethyl, and phenyl. In another alternative of this embodiment, $Z_1$ is $C_1$–$C_8$ alkyl, $C_2$–$C_8$ alkenyl, or $C_2$–$C_8$ alkynyl, the alkyl, alkenyl, or alkynyl being optionally substituted with fluorine, hydroxy, carboxy, or alkoxycarbonyl. In yet another alternative of this embodiment, $Z_1$ is selected from the group consisting of cyclopropyl, isopropyl, methyl, ethyl, cyclobutyl, isobutyl, tert-butyl, sec-butyl, and phenyl optionally substituted at any substitutable position with fluorine, hydroxy, carboxy or alkoxycarbonyl. In yet another alternative of this embodiment, $Z_1$ is propyl, isopropyl, cyclopropyl, tert-butyl and cyclobutyl. In another alternative of this embodiment, $Z_1$ is cyclopropyl or isopropyl optionally substituted at any substitutable position with fluorine, hydroxy, carboxy or alkoxycarbonyl. In still another alternative of this embodiment, $Z_1$ is phenyl optionally substituted with fluorine, hydroxy, carboxy, or alkoxycarbonyl. In yet another alternative of this embodiment, $Z_1$ is trifluoroethyl or carboxymethyl.

In one embodiment of compounds corresponding to formula (1), $Z_2$ is a hydrogen bond acceptor. Generally, hydrogen bond acceptors are heteroatoms that have a lone pair of electrons available for hydrogen bonding. When taken with the carbon to which $Z_2$ is attached, suitable hydrogen bond acceptors are selected from the group consisting of C(O), C(S), C(Cl), C(Br), C(F), C(OH), $COCH_3$, COR, C(SH), CSR, and $CNR_1R_2$ wherein R, $R_1$ and $R_2$ are independently hydrogen, alkyl, aryl, and arylakyl, optionally substituted with halogen, hydroxy or alkoxy.

In one embodiment of compounds corresponding to formula (1), $Z_3$ is a 5- or 6-membered heterocyclic or aromatic ring substituted with an amidine or a derivatized amidine group and may be optionally substituted at any substitutable position with halogen, hydroxy, haloalkyl, alkyl, carboxy, alkoxycarbonyl, or hydrocarbyloxy, or any combination thereof. A preferred halogen is fluorine. In one alternative of this embodiment, directed toward the prodrugs of the compounds of formula (1), the 5- or 6-membered heterocyclic or aromatic ring comprising $Z_3$ is substituted with a derivatized amidine which, upon hydrolysis, oxidation, reduction or elimination, or any combination thereof, yields an amidine group. In another alternative of this embodiment, $Z_3$ is a 6-membered carbocyclic aromatic ring substituted with either an amidine group, or for embodiments directed toward the prodrug, with a derivatized amidine. In yet another embodiment, $Z_3$ comprises a substituted phenyl, thienyl, or furanyl ring, the phenyl, thienyl or furanyl ring being substituted with an amidine or a derivatized amidine group, and optionally further substituted at any substitutable position with fluorine, hydroxy, carboxy, alkoxycarbonyl, or hydrocarbyloxy. For embodiments directed toward the prodrug, the amidine group is derivatized according to any of the embodiments described more thoroughly below. In yet another alternative of this embodiment, $Z_3$ corresponds to formula (a):

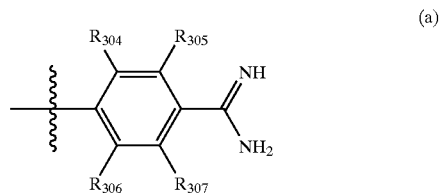

(a)

wherein $R_{304}$ and $R_{306}$ are independently selected from the group consisting of hydrogen, fluorine, hydroxy, carboxy, hydrocarbyloxy and alkoxycarbonyl; and $R_{305}$ and $R_{307}$ are independently selected from the group consisting of hydrogen, fluorine, methoxy, hydroxy and carboxy.

In one alternative of compounds wherein $Z_3$ corresponds to formula (a), $Z_3$ is selected from the group consisting of benzamidine-4-yl, 3-hydroxybenzamidine-4-yl, 3,5-dihydroxybenzamidine-4-yl, 2,5,6-trifluoro-3-hydroxybenzamidine-4-yl, 2-hydroxybenzamidine-4-yl and 3,5,6-trifluoro-2-hydroxybenzamidine-4-yl.

In one embodiment of compounds corresponding to formula (1), $Z_4$ comprises a 5- or 6-membered heterocyclic or carbocyclic ring, the ring atoms of the 5- or 6-membered heterocyclic or carbocyclic ring of $Z_4$ being carbon, nitrogen, oxygen, or sulfur. In one alternative of this embodiment, $Z_4$ comprises a 5- or 6-membered heterocyclic or carbocyclic ring, the ring atoms of $Z_4$ being $Z_{40}$, $Z_{41}$, $Z_{42}$, $Z_{44}$ and $Z_{45}$ when $Z_4$ is a 5-membered ring and $Z_{40}$, $Z_{41}$, $Z_{42}$, $Z_{43}$, $Z_{44}$ and $Z_{45}$ when $Z_4$ is a 6-membered ring, $Z_{40}$, $Z_{41}$, $Z_{42}$, $Z_{43}$, $Z_{44}$ and $Z_{45}$, being carbon, nitrogen, oxygen or sulfur, $Z_{40}$ being the ring atom through which $Z_4$ is attached to the heterocyclic core ring, $Z_{41}$ and $Z_{45}$ each being in an alpha position relative to $Z_{40}$, $Z_{42}$ and $Z_{44}$ each being in a beta position relative to $Z_{40}$, $Z_{43}$ being in the gamma position relative to $Z_{40}$ when $Z_4$ is a 6-membered ring, $Z_4$ having a substituent $R_{42}$ covalently attached to $Z_{42}$, and a second substituent bonded to one of $Z_{41}$, $Z_{43}$, $Z_{44}$, or $Z_{45}$, the substituent being $R_{41}$ when bonded to $Z_{41}$, the substituent being $R_{43}$ when bonded to $Z_{43}$, the substituent being $R_{44}$ when bonded to $Z_{44}$, and the substituent being $R_{45}$ when bonded to $Z_{45}$; $R_{42}$ is amino; and $R_{41}$, $R_{43}$, $R_{44}$ and $R_{45}$ are independently hydrogen, hydrocarbyl, substituted hydrocarbyl, heterocyclo, halogen, or a substituted or unsubstituted heteroatom selected from nitrogen, oxygen, sulfur and phosphorus, provided at least one of $R_{41}$, $R_{43}$, $R_{44}$ or $R_{45}$ is other than hydrogen. In another alternative of this embodiment, $Z_4$ is a substituted, 6-membered, carbocyclic aromatic ring. In another alternative of this embodiment, $Z_4$ corresponds to formula (b):

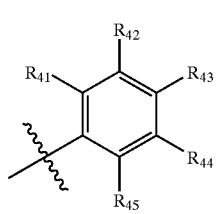

(b)

wherein
$R_{42}$ is amino;
$R_{44}$ is hydrocarbyl, substituted hydrocarbyl, heterocyclo, halogen or a substituted or unsubstituted heteroatom selected from nitrogen, oxygen, sulfur and phosphorus; and $R_{41}$, $R_{43}$ and $R_{45}$ are independently hydrogen, hydrocarbyl, substituted hydrocarbyl, halogen or an optionally substituted heteroatom selected from the group consisting of oxygen, nitrogen, and sulfur.

In one embodiment of compounds wherein $Z_4$ corresponds to formula (b), $R_{44}$ is hydrocarbyl, substituted hydrocarbyl, heteroaryl, heterocyclo, halogen, acetamido, guanidino, hydroxy, nitro, amino, amidosulfonyl, acylamido, hydrocarbyloxy, substituted hydrocarbyloxy, hydrocarbylthio, substituted hydrocarbylthio, hydrocarbylsulfonyl, or substituted hydrocarbylsulfonyl. In one alternative of this embodiment, wherein $Z_4$ corresponds to formula (b), $R_{44}$ is hydroxy, alkylsulfonyl, haloalkyl, carboxamidoalkyl, or carboxamidoalkylaryl. In another alternative of this embodiment, wherein $Z_4$ corresponds to formula (b), $R_{44}$ is selected from the group consisting of hydrocarbyl, substituted hydrocarbyl, acetamidyl, alkoxy, hydroxy, amino, alkylsulfonyl, haloalkoxy, haloalkythio, alkoxycarbonyl, carboxy, sulfonamido, carboxamido and sulfonamidyl, optionally substituted with fluorine. In still another alternative of this embodiment, $R_{44}$ is selected from the group consisting of hydroxy, carboxy, carboxamido, alkoxy, alkylsulfonyl, sulfonamido, and alkoxycarbonyl. In a preferred alternative of this embodiment, $R_{44}$ is sec-butylamide, carboxy, ethoxycarbonyl, isopropoxycarbonyl, butoxycarbonyl, isopropylamide or hydroxy. In yet another alternative of this embodiment, each of $R_{41}$, $R_{43}$ and $R_{45}$ is hydrogen. In still yet another alternative of this embodiment, $Z_{41}$, $Z_{43}$ or $Z_{45}$ is substituted with fluorine or chlorine. In another embodiment of this invention, $R_{44}$ is hydroxy, alkylsulfonyl, haloalkyl, carboxamidoalkyl, or carboxamidoalkylaryl.

In one alternative of compounds wherein $Z_4$ corresponds to formula (b), $R_{42}$ is amino; $R_{43}$ is hydrocarbyl, substituted hydrocarbyl, halogen or an optionally substituted heteroatom selected from the group consisting of oxygen, nitrogen, and sulfur; and $R_{41}$, $R_{44}$ and $R_{45}$ are independently hydrogen, halogen or alkoxy.

In another alternative of compounds wherein $Z_4$ corresponds to formula (b), $R_{42}$ is amino; $R_{45}$ is hydrocarbyl, substituted hydrocarbyl, halogen or an optionally substituted heteroatom selected from the group consisting of oxygen, nitrogen, and sulfur; and $R_{41}$, $R_{43}$ and $R_{44}$ are independently hydrogen, halogen or alkoxy.

In yet another alternative of compounds wherein $Z_4$ corresponds to formula (b), $R_{42}$ is amino; $R_{41}$ is hydrocarbyl, substituted hydrocarbyl, halogen or an optionally substituted heteroatom selected from the group consisting of oxygen, nitrogen, and sulfur; and $R_{43}$, $R_{44}$ and $R_{45}$ are independently hydrogen, halogen or alkoxy.

In an alternative embodiment of compounds of formula (1), $Z_4$ corresponds to formula (c)

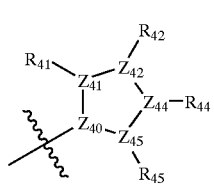

(c)

wherein
$Z_{40}$, $Z_{41}$, $Z_{42}$, $Z_{44}$, and $Z_{45}$ are independently carbon, nitrogen, oxygen or sulfur, and $R_{41}$, $R_{42}$, $R_{44}$, and $R_{45}$ are as defined in connection with the 6-membered carbocylic aromatic ring.

In another aspect of the invention, the compounds of formula (1) may be represented by formula (2):

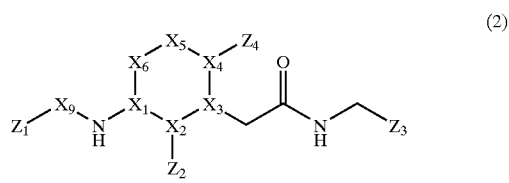

(2)

wherein $X_1$, $X_2$, $X_3$ $X_4$, $X_5$, $X_6$, $Z_1$, $Z_2$, $Z_3$, and $Z_4$ are as described for compounds having structural formula (1) and $X_9$ is a direct bond or $(CH_2)_m$ wherein m is 1 or 2. In one alternative of this embodiment, $X_1$, $X_2$, $X_3$, $X_4$, $X_5$, $X_6$, and $Z_2$ are selected to provide a piperidinone, dihydropyrimidinone, tetrahydropyrimidinone, dehydropiperidinedione, dihydropyridazinone, dihydroisoxazinone, tetrahydrotriazinedione, tetrahydrotriazinone, piperidine, and piperazine heterocyclic ring and $Z_1$, $Z_2$, $Z_3$, and $Z_4$ are as described for formula (1) and $X_9$ is a bond. In another alternative of this embodiment, $X_1$, $X_2$, $X_3$, $X_4$, $X_5$, $X_6$ and $Z_2$ are selected to provide a heterocyclic ring selected from tetrahydrotriazinone, piperidinone, dihydropyrimidinone, tetrahydropyrimidinone, piperidine, and piperazine. In yet another alternative of this embodiment, $X_1$, $X_2$, $X_3$, $X_4$, $X_5$, $X_6$ and $Z_2$ are selected to provide a heterocyclic ring selected from tetrahydrotriazinone, piperidinone, dihydropyrimidinone, and tetrahydropyrimidinone. In a preferred alternative of this embodiment, the heterocyclic ring defined by $X_1$, $X_2$, $X_3$, $X_4$, $X_5$, $X_6$ and $Z_2$ is tetrahydrotriazinone.

In a preferred embodiment of compounds corresponding to formula (2), $X_9$ is a bond; $Z_1$ is selected from the group consisting of cyclopropyl, methyl, ethyl, isobutyl, tert-butyl, and sec-butyl optionally substituted at any substitutable position with fluorine, hydroxy, carboxy, or alkoxycarbonyl; $Z_3$ corresponds to formula (a) and is optionally substituted at any substitutable position with fluorine, hydroxy, carboxy, or hydrocarbyloxy; $Z_4$ corresponds to formula (b) wherein $R_{42}$ is amino and $R_{44}$ is selected from the group consisting of hydrocarbyl, substituted hydrocarbyl, acetamidyl, alkoxy, hydroxy, amino, alkylsulfonyl, haloalkoxy, haloalkythio, alkoxycarbonyl, carboxy, sulfonamido, carboxamido and sulfonamidyl, optionally substituted with fluorine; and $X_1$, $X_2$, $X_3$, $X_4$, $X_5$, $X_6$ and $Z_2$ are as defined above for compounds having formula (1).

In a preferred embodiment, compounds corresponding to formula (2) may be represented by formula (2-a):

(2-a)

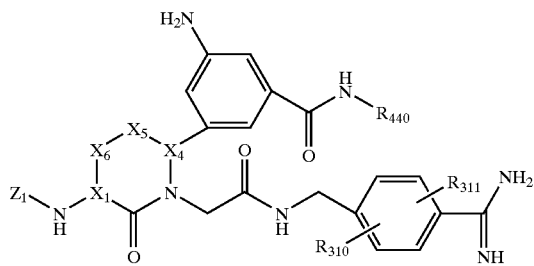

wherein $X_1$, $X_4$, $X_5$ and $X_6$ are independently carbon or nitrogen;

$Z_1$ is selected from the group consisting of cyclopropyl, isopropyl, methyl, ethyl, cyclobutyl, isobutyl, tert-butyl, sec-butyl, and phenyl optionally substituted with fluorine, hydroxy, carboxy, or alkoxycarbonyl;

$R_{440}$ is $C_1$–$C_6$ alkyl, aryl, aralkyl, carboxy, or carboxyalkyl, wherein said alkyl, aryl, aralkyl, carboxy, or carboxyalkyl is optionally further substituted by fluorine; and $R_{310}$ and $R_{311}$ are independently selected from the group consisting of hydrogen, fluorine, hydroxy, alkoxy, and carboxy.

In another preferred embodiment, compounds corresponding to formula (2) may be represented by formula (2-b):

(2-b)

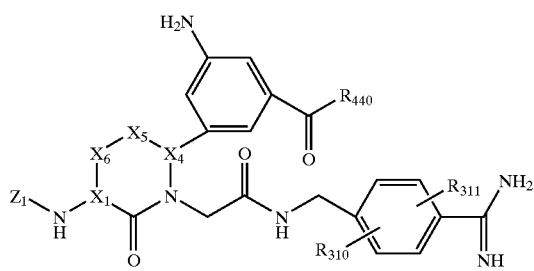

wherein $X_1$, $X_4$, $X_5$ and $X_6$ are independently carbon or nitrogen;

$Z_1$ is selected from the group consisting of cyclopropyl, isopropyl, methyl, ethyl, cyclobutyl, isobutyl, tert-butyl, sec-butyl, and phenyl optionally substituted with fluorine, hydroxy, carboxy, or alkoxycarbonyl;

$R_{440}$ is $C_1$–$C_6$ alkyl, aryl, aralkyl, carboxy, or carboxyalkyl, wherein said alkyl, aryl, aralkyl, carboxy, or carboxyalkyl is optionally further substituted by fluorine; and $R_{310}$ and $R_{311}$ are independently selected from the group consisting of hydrogen, fluorine, hydroxy, alkoxy, and carboxy.

In a preferred alternative of compounds corresponding to formula (2), the compounds possess a tetrahydrotriazinone heterocyclic ring having formula (2-c):

(2-c)

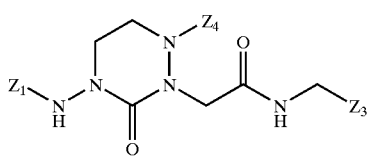

wherein:

$Z_1$, $Z_2$, and $Z_3$ are as defined for compounds having either of formula (1) and formula (2) above.

In one alternative of this embodiment (i.e., compounds having a tetrahydrotriazinone heterocyclic ring core), $Z_1$ is optionally substituted $C_2$ to $C_8$ alkyl, optionally substituted $C_3$ to $C_6$ cycloalkyl and optionally substituted phenyl. Preferred $Z_1$ substituents are optionally substituted cyclopropyl, isopropyl, cyclobutyl, methyl, ethyl and phenyl. In another alternative of this embodiment, $Z_4$ is a substituted, 6-membered, heterocyclic or carbocyclic aromatic ring.

Another aspect of the invention embraces compounds which correspond to formula (1) having the following fused ring formula (3):

(3)

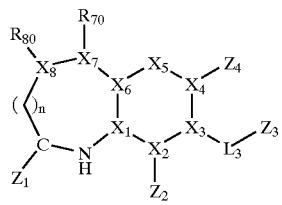

wherein $Z_1$, $Z_2$, $Z_3$, $Z_4$, $L_3$, $X_1$, $X_2$, $X_3$, $X_4$, and $X_5$ are as defined for compounds having formula (1) or (2) above;

$X_6$ is carbon or nitrogen;

$X_7$ and $X_8$ are independently carbon, nitrogen, oxygen or sulfur;

$R_{70}$ and $R_{80}$ are independently selected from the group consisting of hydrogen, halogen, amino, hydrocarbyl, substituted hydrocarbyl, aryl, wherein aryl is phenyl optionally substituted by hydroxy, amino, $C_1$–$C_8$ alkyl, or halogen provided that $R_{70}$ is not present when $X_7$ is a bond and $R_{80}$ is not present when $X_8$ is a bond; or $R_{70}$ and $R_{80}$, along with the ring atoms to which each is attached, form a 5- or 6-membered saturated ring; and n is 0 to 2.

In a preferred embodiment of compounds of formula (3), $L_3$ is $CH_2CONHCH_2$. In one alternative of this embodiment, (i.e., when $L_3$ is $CH_2CONHCH_2$), $X_7$ and $X_8$ are carbon. In another alternative of this embodiment, $Z_3$ corresponds to formula (a) and $Z_4$ corresponds to formula (b).

In another aspect of this invention, compounds corresponding to any of formulas (1), (2), or (3) possess a hydroxy or carboxy substituent at any one of $Z_1$, $Z_2$ or $Z_3$.

In another aspect of this invention for compounds corresponding to any of formulas (1), (2), or (3), $Z_3$ is —$R_{300}C(=NR_{301})NR_{302}R_{303}$, wherein $R_{300}$ is a 6-membered carbocyclic aromatic ring, $R_{301}$, $R_{302}$, $R_{303}$ are independently selected from the group consisting of hydrogen, halogen, optionally substituted hydrocarbyl, and an optionally substituted heteroatom selected from the group consisting of oxygen, nitrogen, phosphorus and sulfur, provided at least one of $R_{301}$, $R_{302}$, $R_{303}$ is other than hydrogen. In yet another alternative of this embodiment, $Z_3$ is —$R_{300}C(=NR_{301})NR_{302}R_{303}$, wherein $R_{300}$ is a 6-membered carbocyclic aromatic ring, and at least two of $R_{301}$, $R_{302}$, $R_{303}$ are ring atoms of a heterocyclic ring. In an alternative of this embodiment, $Z_3$ is —$R_{300}C(=NR_{301})NR_{302}R_{303}$, wherein $R_{300}$ is a 6-membered carbocyclic aromatic ring, and at least one of $R_{301}$, $R_{302}$, $R_{303}$ are ring atoms of a heterocyclic ring fused to $R_{300}$.

In yet another aspect of this invention for compounds corresponding to any of formulas (1), (2), or (3), $Z_3$ is a benzamidine derivatized with one or more groups selected from carbonyl, thiocarbonyl, imino, enamino, phosphorus, and sulfur, where the benzamidine derivative hydrolyzes under physiological conditions to form benzamidine. In a further embodiment, $Z_3$ is a benzamidine derivatized with one or more groups selected from optionally substituted hydrocarbyl, provided that the carbon atom directly bonded to the amidine is sp³ hybridized and aryl, where the benzamidine derivative is oxidized under physiological conditions to form benzamidine. In yet another embodiment, $Z_3$ is a benzamidine derivatized with one or more heteroatoms selected from oxygen, nitrogen in its most reduced state, and sulfur in its most reduced state, where the benzamidine derivative is reduced under physiological conditions to form benzamidine. In still another embodiment, $Z_3$ is a benzamidine derivatized with one or more substituents selected from a hydrocarbyl substituted at the beta carbon with carbonyl, sulfonyl, sulfinyl, cyano, nitro and an alkyl, aryl, or heterocyclic group substituted with oxygen, nitrogen, or sulfur at the carbon directly bonded to the amidine group, where the benzamidine derivative undergoes elimination at physiological conditions to form benzamidine.

In a further embodiment for compounds corresponding to any of formulas (1), (2), or (3), $Z_3$ corresponds to formula (d):

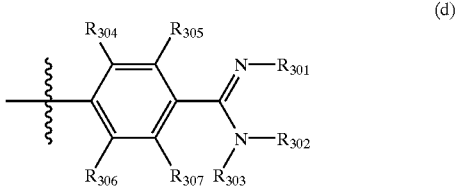

(d)

wherein:
$R_{301}$, $R_{302}$, and $R_{303}$ are independently selected from the group consisting of:
(i) hydrogen, —C(=O)$R_a$, —C(=O)O$R_a$, —S(=O)O$R_a$, —S(=O)S$R_a$, —S(=O)$_2$O$R_a$, —S(=O)$_2$S$R_a$ and alkenyl, wherein $R_a$ is selected from the group consisting of hydrocarbyl, substituted hydrocarbyl, and heterocylo, provided, however, that the carbon atom of $R_{301}$, $R_{302}$, and $R_{303}$ directly bonded to the amidine is sp² hybridized when $R_{301}$, $R_{302}$, and $R_{303}$ is alkenyl,
(ii) hydrogen, optionally substituted hydrocarbyl and aryl, provided, however, the carbon atom of $R_{301}$, $R_{302}$, and $R_{303}$ directly bonded to the amidine is sp³ hybridized when $R_{301}$, $R_{302}$, and $R_{303}$ is optionally substituted hydrocarbyl,
(iii) hydrogen, —O$R_b$, —S$R_b$, —N$R_b$, or —N($R_b$)$_2$, wherein each $R_b$ is independently optionally substituted hydrocarbyl, and heterocylo, and
(iv) hydrogen, substituted hydrocarbyl wherein the carbon bonded to the amidine group is substituted with —O$R_c$, —S$R_c$, —N$R_c$, or —N($R_c$)$_2$, wherein each $R_c$ is independently —C(O)$R_d$, —C(O)N$R_d$, —C(O)O$R_d$, —C(O)N(Rd)$_2$ and each $R_d$ is independently hydrocarbyl, substituted hydrocarbyl or heterocyclo, and substituted alkyl with the carbon atom beta to the point of attachment to the amidine group being an unsaturated electron withdrawing group, provided, however, at least one of $R_{301}$, $R_{302}$, and $R_{303}$ is other than hydrogen;
$R_{304}$ is selected from the group consisting of halogen, hydrogen, hydroxyl, alkyl, sulfhydryl, alkoxy, and alkylthio;
$R_{305}$ is selected from the group consisting of oxygen, sulfur, halogen, hydrogen, hydroxyl, alkyl, sulfhydryl, alkoxy, and alkylthio;
$R_{306}$ is selected from the group consisting of halogen, hydrogen, hydroxyl, alkyl, sulfhydryl, alkoxy, and alkylthio; and
$R_{307}$ is selected from the group consisting of oxygen, sulfur, halogen, hydrogen, hydroxyl, alkyl, sulfhydryl, alkoxy, and alkylthio.

In one embodiment, the benzamidine derivative is hydrolyzed under physiological conditions to form benzamidine when $Z_3$ is a benzamidine derivative having formula (d) and $R_{301}$, $R_{302}$, and $R_{303}$ are independently selected from hydrogen, —C(=O)$R_a$, —C(=O)O$R_a$, —S(=O)O$R_a$, —S(=O)S$R_a$, —S(=O)$_2$O$R_a$, —S(=O)$_2$S$R_a$ and alkenyl, wherein $R_a$ is selected from the group consisting of hydrocarbyl, substituted hydrocarbyl, and heterocylo, provided, however, that the carbon atom of $R_{301}$, $R_{302}$, and $R_{303}$ directly bonded to the amidine is sp² hybridized when $R_{301}$, $R_{302}$, and $R_{303}$ is alkenyl.

In a further embodiment, the benzamidine derivative is oxidized under physiological conditions to form benzamidine when $Z_3$ is a benzamidine derivative having formula (d) and $R_{301}$, $R_{302}$, and $R_{303}$ are independently selected from hydrogen, optionally substituted hydrocarbyl and aryl, provided, however, the carbon atom of $R_{301}$, $R_{302}$, and $R_{303}$ directly bonded to the amidine is Sp³ hybridized when $R_{301}$, $R_{302}$, and $R_{303}$ is optionally substituted hydrocarbyl.

In still another embodiment, the benzamidine derivative is reduced under physiological conditions to form benzamidine when $Z_3$ is a benzamidine derivative having formula (d) and $R_{301}$, $R_{302}$, and $R_{303}$ are independently selected from hydrogen, —O$R_b$, —S$R_b$, —N$R_b$, or —N($R_b$)$_2$, wherein each $R_b$ is independently optionally substituted hydrocarbyl, and heterocylo.

In an alternative embodiment, the benzamidine derivative undergoes elimination at physiological conditions to form benzamidine when $Z_3$ is a benzamidine derivative having formula (d) and $R_{301}$, $R_{302}$, and $R_{303}$ are independently selected from hydrogen, substituted hydrocarbyl wherein the carbon bonded to the amidine group is substituted with —O$R_c$, —S$R_c$, —N$R_c$, or —N($R_c$)$_2$, wherein each $R_c$ is independently —C(O)$R_d$, —C(O)N$R_d$, —C(O)O$R_d$, —C(O)N($R_d$)$_2$ and each $R_d$ is independently hydrocarbyl, substituted hydrocarbyl or heterocyclo, and substituted alkyl with the carbon atom beta to the point of attachment to the amidine group being an unsaturated electron withdrawing group.

Another aspect of the invention embraces intermediate compounds having either of two formulae. Compounds corresponding to one of the formulae may be represented by formula (4):

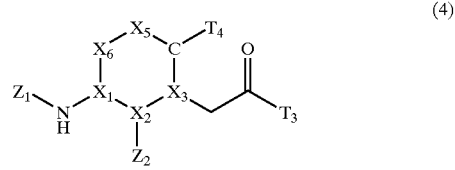

(4)

wherein
$X_1$, $X_2$, $X_5$, and $X_6$ are members of a heterocyclic ring;
$X_1$, $X_2$ and $X_3$ are independently carbon or nitrogen;
$X_5$ and $X_6$ are independently selected from the group consisting of nitrogen, oxygen, sulfur, carbon, C(F) and C(Br);
provided no more than 4 of $X_1$, $X_2$, $X_3$, $X_4$, $X_5$, and $X_6$ are sp² hybridized;
$Z_1$ is hydrocarbyl, or substituted hydrocarbyl;
$Z_2$ is a hydrogen bond acceptor covalently or datively bonded to $X_2$;
$T_3$ is selected from the group consisting of hydroxy, alkoxy, substituted alkoxy, and substituted amino; and
$T_4$ is selected from the group consisting of —Cl, —Br, —I, —S(CH$_3$), and —OSO$_2$(CF$_3$).

Intermediate compounds represented by the other formula correspond to formula (5):

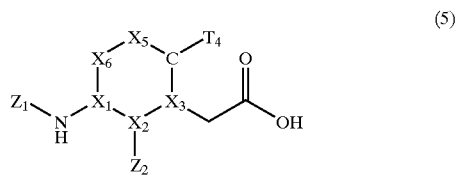

(5)

wherein $X_1$, $X_2$, $X_5$, and $X_6$ are members of a heterocyclic ring;

$X_1$, $X_2$ and $X_3$ are independently carbon or nitrogen;

$X_5$ and $X_6$ are independently selected from the group consisting of nitrogen, oxygen, sulfur, carbon, C(F) and C(Br);

provided no more than 4 of $X_1$, $X_2$, $X_3$, $X_4$, $X_5$, and $X_6$ are $sp^2$ hybridized;

$Z_1$ is hydrocarbyl, or substituted hydrocarbyl;

$Z_2$ is a hydrogen bond acceptor covalently or datively bonded to $X_2$; and $Z_4$ comprises hydrocarbyl, substituted hydrocarbyl or a 5- or 6-membered heterocyclic or carbocyclic ring, the ring atoms of the 5 or 6 membered heterocyclic or carboxylic ring of $Z_4$ being carbon, nitrogen, oxygen, or sulfur.

Among the preferred embodiments, therefore, are compounds corresponding to any one of formulas (1), (2), or (3) wherein $X_9$ is a direct bond, $Z_4$ is a substituted, 6-membered, carbocyclic aromatic ring, $Z_3$ is benzene substituted with an amidine or a derivatized amidine group which, upon hydrolysis, oxidation, reduction or elimination under physiological conditions yields an amidine group, and $Z_1$ is selected from the group consisting of cyclopropyl, isopropyl, methyl, cyclobutyl, trifluoroethyl, carboxymethyl and phenyl. In an alternative of this embodiment, $Z_4$ is phenyl substituted with two substituents, $R_{42}$ and $R_{44}$ wherein $R_{42}$ and $R_{44}$ are as described for any of formulas (1), (2), or (3).

Following the processes described in the Schemes, Examples or elsewhere herein, compounds corresponding to each of formulae A, B, C, and D and having any of the combinations of substituents identified in Table 1 may be prepared.

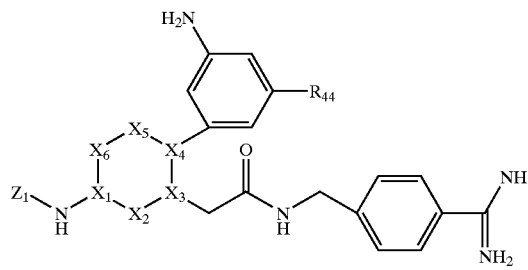

(A)

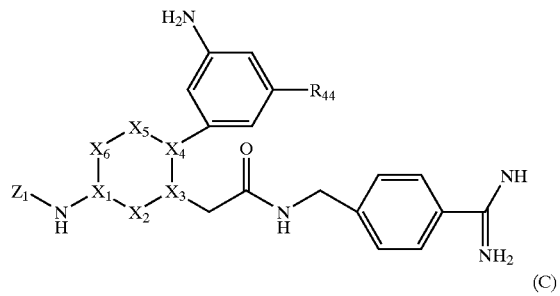

(B)

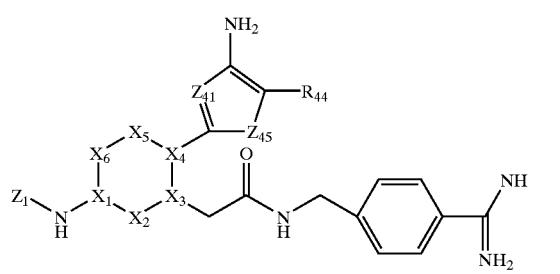

(C)

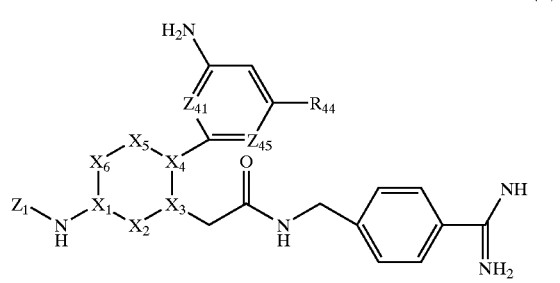

(D)

wherein $X_1$, $X_2$, $X_3$, $X_4$, $X_5$, and $X_6$ are selected to provide the following heterocyclic rings: piperidinone, dihydropyrimidinone, tetrahydropyrimidinone, dehydropiperidinedione, dihydropyridazinone, dihydroisoxazinone, tetrahydrotriazinedione, tetrahydrotriazinone, piperidine, and piperazine and, for structure (C), one of $Z_{41}$ and $Z_{45}$ is sulfur while the other is carbon and, for structure (D), one of $Z_{41}$ and $Z_{45}$ is nitrogen while the other is carbon. As employed herein, unless otherwise indicated, "core" refers to the 6-membered ring to which $Z_1$, $Z_3$ and $Z_4$, through their respective linkages, are attached.

TABLE 1

| Core | $Z_1$ | $R_{44}$ |
|---|---|---|
| Piperidinone | substituted alkyl | hydroxy |
| Piperidinone | substituted alkyl | isobutylsulfonyl |
| Piperidinone | substituted alkyl | trifluoromethyl |
| Piperidinone | substituted alkyl | carboxamidobenzyl |
| Piperidinone | substituted alkyl | carboxamidobutyl-2-yl |
| Piperidinone | substituted alkyl | isobutyramido |
| Piperidinone | substituted alkyl | isobutoxy |
| Piperidinone | substituted alkyl | carboethoxy |

TABLE 1-continued

| Core | $Z_1$ | $R_{44}$ |
|---|---|---|
| Piperidinone | substituted alkyl | carboxyl |
| Piperidinone | substituted alkyl | amino |
| Dihydropyrimidinone | substituted alkyl | hydroxy |
| Dihydropyrimidinone | substituted alkyl | isobutylsulfonyl |
| Dihydropyrimidinone | substituted alkyl | trifluoromethyl |
| Dihydropyrimidinone | substituted alkyl | carboxamidobenzyl |
| Dihydropyrimidinone | substituted alkyl | carboxamidobutyl-2-yl |
| Dihydropyrimidinone | substituted alkyl | isobutyramido |
| Dihydropyrimidinone | substituted alkyl | isobutoxy |
| Dihydropyrimidinone | substituted alkyl | carboethoxy |
| Dihydropyrimidinone | substituted alkyl | carboxyl |
| Dihydropyrimidinone | substituted alkyl | amino |
| Tetrahydropyrimidinone | substituted alkyl | hydroxy |
| Tetrahydropyrimidinone | substituted alkyl | isobutylsulfonyl |
| Tetrahydropyrimidinone | substituted alkyl | trifluoromethyl |
| Tetrahydropyrimidinone | substituted alkyl | carboxamidobenzyl |
| Tetrahydropyrimidinone | substituted alkyl | carboxamidobutyl-2-yl |
| Tetrahydropyrimidinone | substituted alkyl | isobutyramido |
| Tetrahydropyrimidinone | substituted alkyl | isobutoxy |
| Tetrahydropyrimidinone | substituted alkyl | carboethoxy |
| Tetrahydropyrimidinone | substituted alkyl | carboxyl |
| Tetrahydropyrimidinone | substituted alkyl | amino |
| Dehydropiperidinedione | substituted alkyl | hydroxy |
| Dehydropiperidinedione | substituted alkyl | isobutylsulfonyl |
| Dehydropiperidinedione | substituted alkyl | trifluoromethyl |
| Dehydropiperidinedione | substituted alkyl | carboxamidobenzyl |
| Dehydropiperidinedione | substituted alkyl | carboxamidobutyl-2-yl |
| Dehydropiperidinedione | substituted alkyl | isobutyramido |
| Dehydropiperidinedione | substituted alkyl | isobutoxy |
| Dehydropiperidinedione | substituted alkyl | carboethoxy |
| Dehydropiperidinedione | substituted alkyl | carboxyl |
| Dehydropiperidinedione | substituted alkyl | amino |
| Dihydropyridazinone | substituted alkyl | hydroxy |
| Dihydropyridazinone | substituted alkyl | isobutylsulfonyl |
| Dihydropyridazinone | substituted alkyl | trifluoromethyl |
| Dihydropyridazinone | substituted alkyl | carboxamidobenzyl |
| Dihydropyridazinone | substituted alkyl | carboxamidobutyl-2-yl |
| Dihydropyridazinone | substituted alkyl | isobutyramido |
| Dihydropyridazinone | substituted alkyl | isobutoxy |
| Dihydropyridazinone | substituted alkyl | carboethoxy |
| Dihydropyridazinone | substituted alkyl | carboxyl |
| Dihydropyridazinone | substituted alkyl | amino |
| Dihydroisoxazinone | substituted alkyl | hydroxy |
| Dihydroisoxazinone | substituted alkyl | isobutylsulfonyl |
| Dihydroisoxazinone | substituted alkyl | trifluoromethyl |
| Dihydroisoxazinone | substituted alkyl | carboxamidobenzyl |
| Dihydroisoxazinone | substituted alkyl | carboxamidobutyl-2-yl |
| Dihydroisoxazinone | substituted alkyl | isobutyramido |
| Dihydroisoxazinone | substituted alkyl | isobutoxy |
| Dihydroisoxazinone | substituted alkyl | carboethoxy |
| Dihydroisoxazinone | substituted alkyl | carboxyl |
| Dihydroisoxazinone | substituted alkyl | amino |
| Tetrahydrotriazinedione | substituted alkyl | hydroxy |
| Tetrahydrotriazinedione | substituted alkyl | isobutylsulfonyl |
| Tetrahydrotriazinedione | substituted alkyl | trifluoromethyl |
| Tetrahydrotriazinedione | substituted alkyl | carboxamidobenzyl |
| Tetrahydrotriazinedione | substituted alkyl | carboxamidobutyl-2-yl |
| Tetrahydrotriazinedione | substituted alkyl | isobutyramido |
| Tetrahydrotriazinedione | substituted alkyl | isobutoxy |
| Tetrahydrotriazinedione | substituted alkyl | carboethoxy |
| Tetrahydrotriazinedione | substituted alkyl | carboxyl |
| Tetrahydrotriazinedione | substituted alkyl | amino |
| Tetrahydrotriazinone | substituted alkyl | hydroxy |
| Tetrahydrotriazinone | substituted alkyl | isobutylsulfonyl |
| Tetrahydrotriazinone | substituted alkyl | trifluoromethyl |
| Tetrahydrotriazinone | substituted alkyl | carboxamidobenzyl |
| Tetrahydrotriazinone | substituted alkyl | carboxamidobutyl-2-yl |
| Tetrahydrotriazinone | substituted alkyl | isobutyramido |
| Tetrahydrotriazinone | substituted alkyl | isobutoxy |
| Tetrahydrotriazinone | substituted alkyl | carboethoxy |
| Tetrahydrotriazinone | substituted alkyl | carboxyl |
| Tetrahydrotriazinone | substituted alkyl | amino |
| Piperidine | substituted alkyl | hydroxy |
| Piperidine | substituted alkyl | isobutylsulfonyl |
| Piperidine | substituted alkyl | trifluoromethyl |
| Piperidine | substituted alkyl | carboxamidobenzyl |

TABLE 1-continued

| Core | $Z_1$ | $R_{44}$ |
|---|---|---|
| Piperidine | substituted alkyl | carboxamidobutyl-2-yl |
| Piperidine | substituted alkyl | isobutyramido |
| Piperidine | substituted alkyl | isobutoxy |
| Piperidine | substituted alkyl | carboethoxy |
| Piperidine | substituted alkyl | carboxyl |
| Piperidine | substituted alkyl | amino |
| Piperazine | substituted alkyl | hydroxy |
| Piperazine | substituted alkyl | isobutylsulfonyl |
| Piperazine | substituted alkyl | trifluoromethyl |
| Piperazine | substituted alkyl | carboxamidobenzyl |
| Piperazine | substituted alkyl | carboxamidobutyl-2-yl |
| Piperazine | substituted alkyl | isobutyramido |
| Piperazine | substituted alkyl | isobutoxy |
| Piperazine | substituted alkyl | carboethoxy |
| Piperazine | substituted alkyl | carboxyl |
| Piperazine | substituted alkyl | amino |
| Piperidinone | alkyl | hydroxy |
| Piperidinone | alkyl | isobutylsulfonyl |
| Piperidinone | alkyl | trifluoromethyl |
| Piperidinone | alkyl | carboxamidobenzyl |
| Piperidinone | alkyl | carboxamidobutyl-2-yl |
| Piperidinone | alkyl | isobutyramido |
| Piperidinone | alkyl | isobutoxy |
| Piperidinone | alkyl | carboethoxy |
| Piperidinone | alkyl | carboxyl |
| Piperidinone | alkyl | amino |
| Dihydropyrimidinone | alkyl | hydroxy |
| Dihydropyrimidinone | alkyl | isobutylsulfonyl |
| Dihydropyrimidinone | alkyl | trifluoromethyl |
| Dihydropyrimidinone | alkyl | carboxamidobenzyl |
| Dihydropyrimidinone | alkyl | carboxamidobutyl-2-yl |
| Dihydropyrimidinone | alkyl | isobutyramido |
| Dihydropyrimidinone | alkyl | isobutoxy |
| Dihydropyrimidinone | alkyl | carboethoxy |
| Dihydropyrimidinone | alkyl | carboxyl |
| Dihydropyrimidinone | alkyl | amino |
| Tetrahydropyrimidinone | alkyl | hydroxy |
| Tetrahydropyrimidinone | alkyl | isobutylsulfonyl |
| Tetrahydropyrimidinone | alkyl | trifluoromethyl |
| Tetrahydropyrimidinone | alkyl | carboxamidobenzyl |
| Tetrahydropyrimidinone | alkyl | carboxamidobutyl-2-yl |
| Tetrahydropyrimidinone | alkyl | isobutyramido |
| Tetrahydropyrimidinone | alkyl | isobutoxy |
| Tetrahydropyrimidinone | alkyl | carboethoxy |
| Tetrahydropyrimidinone | alkyl | carboxyl |
| Tetrahydropyrimidinone | alkyl | amino |
| Dehydropiperidinedione | alkyl | hydroxy |
| Dehydropiperidinedione | alkyl | isobutylsulfonyl |
| Dehydropiperidinedione | alkyl | trifluoromethyl |
| Dehydropiperidinedione | alkyl | carboxamidobenzyl |
| Dehydropiperidinedione | alkyl | carboxamidobutyl-2-yl |
| Dehydropiperidinedione | alkyl | isobutyramido |
| Dehydropiperidinedione | alkyl | isobutoxy |
| Dehydropiperidinedione | alkyl | carboethoxy |
| Dehydropiperidinedione | alkyl | carboxyl |
| Dehydropiperidinedione | alkyl | amino |
| Dihydropyridazinone | alkyl | hydroxy |
| Dihydropyridazinone | alkyl | isobutylsulfonyl |
| Dihydropyridazinone | alkyl | trifluoromethyl |
| Dihydropyridazinone | alkyl | carboxamidobenzyl |
| Dihydropyridazinone | alkyl | carboxamidobutyl-2-yl |
| Dihydropyridazinone | alkyl | isobutyramido |
| Dihydropyridazinone | alkyl | isobutoxy |
| Dihydropyridazinone | alkyl | carboethoxy |
| Dihydropyridazinone | alkyl | carboxyl |
| Dihydropyridazinone | alkyl | amino |
| Dihydroisoxazinone | alkyl | hydroxy |
| Dihydroisoxazinone | alkyl | isobutylsulfonyl |
| Dihydroisoxazinone | alkyl | trifluoromethyl |
| Dihydroisoxazinone | alkyl | carboxamidobenzyl |
| Dihydroisoxazinone | alkyl | carboxamidobutyl-2-yl |
| Dihydroisoxazinone | alkyl | isobutyramido |
| Dihydroisoxazinone | alkyl | isobutoxy |
| Dihydroisoxazinone | alkyl | carboethoxy |
| Dihydroisoxazinone | alkyl | carboxyl |
| Dihydroisoxazinone | alkyl | amino |
| Tetrahydrotriazinedione | alkyl | hydroxy |
| Tetrahydrotriazinedione | alkyl | isobutylsulfonyl |
| Tetrahydrotriazinedione | alkyl | trifluoromethyl |
| Tetrahydrotriazinedione | alkyl | carboxamidobenzyl |
| Tetrahydrotriazinedione | alkyl | carboxamidobutyl-2-yl |
| Tetrahydrotriazinedione | alkyl | isobutyramido |
| Tetrahydrotriazinedione | alkyl | isobutoxy |
| Tetrahydrotriazinedione | alkyl | carboethoxy |
| Tetrahydrotriazinedione | alkyl | carboxyl |
| Tetrahydrotriazinedione | alkyl | amino |
| Tetrahydrotriazinone | alkyl | hydroxy |
| Tetrahydrotriazinone | alkyl | isobutylsulfonyl |
| Tetrahydrotriazinone | alkyl | trifluoromethyl |
| Tetrahydrotriazinone | alkyl | carboxamidobenzyl |
| Tetrahydrotriazinone | alkyl | carboxamidobutyl-2-yl |
| Tetrahydrotriazinone | alkyl | isobutyramido |
| Tetrahydrotriazinone | alkyl | isobutoxy |
| Tetrahydrotriazinone | alkyl | carboethoxy |
| Tetrahydrotriazinone | alkyl | carboxyl |
| Tetrahydrotriazinone | alkyl | amino |
| Piperidine | alkyl | hydroxy |
| Piperidine | alkyl | isobutylsulfonyl |
| Piperidine | alkyl | trifluoromethyl |
| Piperidine | alkyl | carboxamidobenzyl |
| Piperidine | alkyl | carboxamidobutyl-2-yl |
| Piperidine | alkyl | isobutyramido |
| Piperidine | alkyl | isobutoxy |
| Piperidine | alkyl | carboethoxy |
| Piperidine | alkyl | carboxyl |
| Piperidine | alkyl | amino |
| Piperazine | alkyl | hydroxy |
| Piperazine | alkyl | isobutylsulfonyl |
| Piperazine | alkyl | trifluoromethyl |
| Piperazine | alkyl | carboxamidobenzyl |
| Piperazine | alkyl | carboxamidobutyl-2-yl |
| Piperazine | alkyl | isobutyramido |
| Piperazine | alkyl | isobutoxy |
| Piperazine | alkyl | carboethoxy |
| Piperazine | alkyl | carboxyl |
| Piperazine | alkyl | amino |
| Piperidinone | substituted phenyl | hydroxy |
| Piperidinone | substituted phenyl | isobutylsulfonyl |
| Piperidinone | substituted phenyl | trifluoromethyl |
| Piperidinone | substituted phenyl | carboxamidobenzyl |
| Piperidinone | substituted phenyl | carboxamidobutyl-2-yl |
| Piperidinone | substituted phenyl | isobutyramido |
| Piperidinone | substituted phenyl | isobutoxy |
| Piperidinone | substituted phenyl | carboethoxy |
| Piperidinone | substituted phenyl | carboxyl |
| Piperidinone | substituted phenyl | amino |
| Dihydropyrimidinone | substituted phenyl | hydroxy |

TABLE 1-continued

| Core | $Z_1$ | $R_{44}$ |
|---|---|---|
| Dihydropyrimidinone | substituted phenyl | isobutylsulfonyl |
| Dihydropyrimidinone | substituted phenyl | trifluoromethyl |
| Dihydropyrimidinone | substituted phenyl | carboxamidobenzyl |
| Dihydropyrimidinone | substituted phenyl | carboxamidobutyl-2-yl |
| Dihydropyrimidinone | substituted phenyl | isobutyramido |
| Dihydropyrimidinone | substituted phenyl | isobutoxy |
| Dihydropyrimidinone | substituted phenyl | carboethoxy |
| Dihydropyrimidinone | substituted phenyl | carboxyl |
| Dihydropyrimidinone | substituted phenyl | amino |
| Tetrahydropyrimidinone | substituted phenyl | hydroxy |
| Tetrahydropyrimidinone | substituted phenyl | isobutylsulfonyl |
| Tetrahydropyrimidinone | substituted phenyl | trifluoromethyl |
| Tetrahydropyrimidinone | substituted phenyl | carboxamidobenzyl |
| Tetrahydropyrimidinone | substituted phenyl | carboxamidobutyl-2-yl |
| Tetrahydropyrimidinone | substituted phenyl | isobutyramido |
| Tetrahydropyrimidinone | substituted phenyl | isobutoxy |
| Tetrahydropyrimidinone | substituted phenyl | carboethoxy |
| Tetrahydropyrimidinone | substituted phenyl | carboxyl |
| Tetrahydropyrimidinone | substituted phenyl | amino |
| Dehydropiperidinedione | substituted phenyl | hydroxy |
| Dehydropiperidinedione | substituted phenyl | isobutylsulfonyl |
| Dehydropiperidinedione | substituted phenyl | trifluoromethyl |
| Dehydropiperidinedione | substituted phenyl | carboxamidobenzyl |
| Dehydropiperidinedione | substituted phenyl | carboxamidobutyl-2-yl |
| Dehydropiperidinedione | substituted phenyl | isobutyramido |
| Dehydropiperidinedione | substituted phenyl | isobutoxy |
| Dehydropiperidinedione | substituted phenyl | carboethoxy |
| Dehydropiperidinedione | substituted phenyl | carboxyl |
| Dehydropiperidinedione | substituted phenyl | amino |
| Dihydropyridazinone | substituted phenyl | hydroxy |
| Dihydropyridazinone | substituted phenyl | isobutylsulfonyl |
| Dihydropyridazinone | substituted phenyl | trifluoromethyl |
| Dihydropyridazinone | substituted phenyl | carboxamidobenzyl |
| Dihydropyridazinone | substituted phenyl | carboxamidobutyl-2-yl |
| Dihydropyridazinone | substituted phenyl | isobutyramido |
| Dihydropyridazinone | substituted phenyl | isobutoxy |
| Dihydropyridazinone | substituted phenyl | carboethoxy |
| Dihydropyridazinone | substituted phenyl | carboxyl |
| Dihydropyridazinone | substituted phenyl | amino |
| Dihydroisoxazinone | substituted phenyl | hydroxy |
| Dihydroisoxazinone | substituted phenyl | isobutylsulfonyl |
| Dihydroisoxazinone | substituted phenyl | trifluoromethyl |
| Dihydroisoxazinone | substituted phenyl | carboxamidobenzyl |
| Dihydroisoxazinone | substituted phenyl | carboxamidobutyl-2-yl |
| Dihydroisoxazinone | substituted phenyl | isobutyramido |
| Dihydroisoxazinone | substituted phenyl | isobutoxy |
| Dihydroisoxazinone | substituted phenyl | carboethoxy |
| Dihydroisoxazinone | substituted phenyl | carboxyl |
| Dihydroisoxazinone | substituted phenyl | amino |
| Tetrahydrotriazinedione | substituted phenyl | hydroxy |
| Tetrahydrotriazinedione | substituted phenyl | isobutylsulfonyl |
| Tetrahydrotriazinedione | substituted phenyl | trifluoromethyl |
| Tetrahydrotriazinedione | substituted phenyl | carboxamidobenzyl |
| Tetrahydrotriazinedione | substituted phenyl | carboxamidobutyl-2-yl |
| Tetrahydrotriazinedione | substituted phenyl | isobutyramido |
| Tetrahydrotriazinedione | substituted phenyl | isobutoxy |
| Tetrahydrotriazinedione | substituted phenyl | carboethoxy |
| Tetrahydrotriazinedione | substituted phenyl | carboxyl |
| Tetrahydrotriazinedione | substituted phenyl | amino |
| Tetrahydrotriazinone | substituted phenyl | hydroxy |
| Tetrahydrotriazinone | substituted phenyl | isobutylsulfonyl |
| Tetrahydrotriazinone | substituted phenyl | trifluoromethyl |
| Tetrahydrotriazinone | substituted phenyl | carboxamidobenzyl |
| Tetrahydrotriazinone | substituted phenyl | carboxamidobutyl-2-yl |
| Tetrahydrotriazinone | substituted phenyl | isobutyramido |
| Tetrahydrotriazinone | substituted phenyl | isobutoxy |
| Tetrahydrotriazinone | substituted phenyl | carboethoxy |
| Tetrahydrotriazinone | substituted phenyl | carboxyl |
| Tetrahydrotriazinone | substituted phenyl | amino |
| Piperidine | substituted phenyl | hydroxy |
| Piperidine | substituted phenyl | isobutylsulfonyl |
| Piperidine | substituted phenyl | trifluoromethyl |
| Piperidine | substituted phenyl | carboxamidobenzyl |
| Piperidine | substituted phenyl | carboxamidobutyl-2-yl |
| Piperidine | substituted phenyl | isobutyramido |
| Piperidine | substituted phenyl | isobutoxy |

TABLE 1-continued

| Core | $Z_1$ | $R_{44}$ |
|---|---|---|
| Piperidine | substituted phenyl | carboethoxy |
| Piperidine | substituted phenyl | carboxyl |
| Piperidine | substituted phenyl | amino |
| Piperazine | substituted phenyl | hydroxy |
| Piperazine | substituted phenyl | isobutylsulfonyl |
| Piperazine | substituted phenyl | trifluoromethyl |
| Piperazine | substituted phenyl | carboxamidobenzyl |
| Piperazine | substituted phenyl | carboxamidobutyl-2-yl |
| Piperazine | substituted phenyl | isobutyramido |
| Piperazine | substituted phenyl | isobutoxy |
| Piperazine | substituted phenyl | carboethoxy |
| Piperazine | substituted phenyl | carboxyl |
| Piperazine | substituted phenyl | amino |
| Piperidinone | phenyl | hydroxy |
| Piperidinone | phenyl | isobutylsulfonyl |
| Piperidinone | phenyl | trifluoromethyl |
| Piperidinone | phenyl | carboxamidobenzyl |
| Piperidinone | phenyl | carboxamidobutyl-2-yl |
| Piperidinone | phenyl | isobutyramido |
| Piperidinone | phenyl | isobutoxy |
| Piperidinone | phenyl | carboethoxy |
| Piperidinone | phenyl | carboxyl |
| Piperidinone | phenyl | amino |
| Dihydropyrimidinone | phenyl | hydroxy |
| Dihydropyrimidinone | phenyl | isobutylsulfonyl |
| Dihydropyrimidinone | phenyl | trifluoromethyl |
| Dihydropyrimidinone | phenyl | carboxamidobenzyl |
| Dihydropyrimidinone | phenyl | carboxamidobutyl-2-yl |
| Dihydropyrimidinone | phenyl | isobutyramido |
| Dihydropyrimidinone | phenyl | isobutoxy |
| Dihydropyrimidinone | phenyl | carboethoxy |
| Dihydropyrimidinone | phenyl | carboxyl |
| Dihydropyrimidinone | phenyl | amino |
| Tetrahydropyrimidinone | phenyl | hydroxy |
| Tetrahydropyrimidinone | phenyl | isobutylsulfonyl |
| Tetrahydropyrimidinone | phenyl | trifluoromethyl |
| Tetrahydropyrimidinone | phenyl | carboxamidobenzyl |
| Tetrahydropyrimidinone | phenyl | carboxamidobutyl-2-yl |
| Tetrahydropyrimidinone | phenyl | isobutyramido |
| Tetrahydropyrimidinone | phenyl | isobutoxy |
| Tetrahydropyrimidinone | phenyl | carboethoxy |
| Tetrahydropyrimidinone | phenyl | carboxyl |
| Tetrahydropyrimidinone | phenyl | amino |
| Dehydropiperidinedione | phenyl | hydroxy |
| Dehydropiperidinedione | phenyl | isobutylsulfonyl |
| Dehydropiperidinedione | phenyl | trifluoromethyl |
| Dehydropiperidinedione | phenyl | carboxamidobenzyl |
| Dehydropiperidinedione | phenyl | carboxamidobutyl-2-yl |
| Dehydropiperidinedione | phenyl | isobutyramido |
| Dehydropiperidinedione | phenyl | isobutoxy |
| Dehydropiperidinedione | phenyl | carboethoxy |
| Dehydropiperidinedione | phenyl | carboxyl |
| Dehydropiperidinedione | phenyl | amino |
| Dihydropyridazinone | phenyl | hydroxy |
| Dihydropyridazinone | phenyl | isobutylsulfonyl |
| Dihydropyridazinone | phenyl | trifluoromethyl |
| Dihydropyridazinone | phenyl | carboxamidobenzyl |
| Dihydropyridazinone | phenyl | carboxamidobutyl-2-yl |
| Dihydropyridazinone | phenyl | isobutyramido |
| Dihydropyridazinone | phenyl | isobutoxy |
| Dihydropyridazinone | phenyl | carboethoxy |
| Dihydropyridazinone | phenyl | carboxyl |
| Dihydropyridazinone | phenyl | amino |
| Dihydroisoxazinone | phenyl | hydroxy |
| Dihydroisoxazinone | phenyl | isobutylsulfonyl |
| Dihydroisoxazinone | phenyl | trifluoromethyl |
| Dihydroisoxazinone | phenyl | carboxamidobenzyl |
| Dihydroisoxazinone | phenyl | carboxamidobutyl-2-yl |
| Dihydroisoxazinone | phenyl | isobutyramido |
| Dihydroisoxazinone | phenyl | isobutoxy |
| Dihydroisoxazinone | phenyl | carboethoxy |
| Dihydroisoxazinone | phenyl | carboxyl |
| Dihydroisoxazinone | phenyl | amino |
| Tetrahydrotriazinedione | phenyl | hydroxy |
| Tetrahydrotriazinedione | phenyl | isobutylsulfonyl |
| Tetrahydrotriazinedione | phenyl | trifluoromethyl |
| Tetrahydrotriazinedione | phenyl | carboxamidobenzyl |
| Tetrahydrotriazinedione | phenyl | carboxamidobutyl-2-yl |
| Tetrahydrotriazinedione | phenyl | isobutyramido |
| Tetrahydrotriazinedione | phenyl | isobutoxy |
| Tetrahydrotriazinedione | phenyl | carboethoxy |
| Tetrahydrotriazinedione | phenyl | carboxyl |
| Tetrahydrotriazinedione | phenyl | amino |
| Tetrahydrotriazinone | phenyl | hydroxy |
| Tetrahydrotriazinone | phenyl | isobutylsulfonyl |
| Tetrahydrotriazinone | phenyl | trifluoromethyl |
| Tetrahydrotriazinone | phenyl | carboxamidobenzyl |
| Tetrahydrotriazinone | phenyl | carboxamidobutyl-2-yl |
| Tetrahydrotriazinone | phenyl | isobutyramido |
| Tetrahydrotriazinone | phenyl | isobutoxy |
| Tetrahydrotriazinone | phenyl | carboethoxy |
| Tetrahydrotriazinone | phenyl | carboxyl |
| Tetrahydrotriazinone | phenyl | amino |
| Piperidine | phenyl | hydroxy |
| Piperidine | phenyl | isobutylsulfonyl |
| Piperidine | phenyl | trifluoromethyl |
| Piperidine | phenyl | carboxamidobenzyl |
| Piperidine | phenyl | carboxamidobutyl-2-yl |
| Piperidine | phenyl | isobutyramido |
| Piperidine | phenyl | isobutoxy |
| Piperidine | phenyl | carboethoxy |
| Piperidine | phenyl | carboxyl |
| Piperidine | phenyl | amino |
| Piperazine | phenyl | hydroxy |
| Piperazine | phenyl | isobutylsulfonyl |
| Piperazine | phenyl | trifluoromethyl |
| Piperazine | phenyl | carboxamidobenzyl |
| Piperazine | phenyl | carboxamidobutyl-2-yl |
| Piperazine | phenyl | isobutyramido |
| Piperazine | phenyl | isobutoxy |
| Piperazine | phenyl | carboethoxy |
| Piperazine | phenyl | carboxyl |
| Piperazine | phenyl | amino |
| Piperidinone | cycloalkyl | hydroxy |
| Piperidinone | cycloalkyl | isobutylsulfonyl |
| Piperidinone | cycloalkyl | trifluoromethyl |
| Piperidinone | cycloalkyl | carboxamidobenzyl |
| Piperidinone | cycloalkyl | carboxamidobutyl-2-yl |
| Piperidinone | cycloalkyl | isobutyramido |
| Piperidinone | cycloalkyl | isobutoxy |
| Piperidinone | cycloalkyl | carboethoxy |
| Piperidinone | cycloalkyl | carboxyl |
| Piperidinone | cycloalkyl | amino |
| Dihydropyrimidinone | cycloalkyl | hydroxy |
| Dihydropyrimidinone | cycloalkyl | isobutylsulfonyl |
| Dihydropyrimidinone | cycloalkyl | trifluoromethyl |
| Dihydropyrimidinone | cycloalkyl | carboxamidobenzyl |
| Dihydropyrimidinone | cycloalkyl | carboxamidobutyl-2-yl |
| Dihydropyrimidinone | cycloalkyl | isobutyramido |
| Dihydropyrimidinone | cycloalkyl | isobutoxy |
| Dihydropyrimidinone | cycloalkyl | carboethoxy |
| Dihydropyrimidinone | cycloalkyl | carboxyl |
| Dihydropyrimidinone | cycloalkyl | amino |
| Tetrahydropyrimidinone | cycloalkyl | hydroxy |
| Tetrahydropyrimidinone | cycloalkyl | isobutylsulfonyl |
| Tetrahydropyrimidinone | cycloalkyl | trifluoromethyl |
| Tetrahydropyrimidinone | cycloalkyl | carboxamidobenzyl |
| Tetrahydropyrimidinone | cycloalkyl | carboxamidobutyl-2-yl |
| Tetrahydropyrimidinone | cycloalkyl | isobutyramido |
| Tetrahydropyrimidinone | cycloalkyl | isobutoxy |
| Tetrahydropyrimidinone | cycloalkyl | carboethoxy |

TABLE 1-continued

| Core | $Z_1$ | $R_{44}$ |
|---|---|---|
| Tetrahydropyrimidinone | cycloalkyl | carboxyl |
| Tetrahydropyrimidinone | cycloalkyl | amino |
| Dehydropiperidinedione | cycloalkyl | hydroxy |
| Dehydropiperidinedione | cycloalkyl | isobutylsulfonyl |
| Dehydropiperidinedione | cycloalkyl | trifluoromethyl |
| Dehydropiperidinedione | cycloalkyl | carboxamidobenzyl |
| Dehydropiperidinedione | cycloalkyl | carboxamidobutyl-2-yl |
| Dehydropiperidinedione | cycloalkyl | isobutyramido |
| Dehydropiperidinedione | cycloalkyl | isobutoxy |
| Dehydropiperidinedione | cycloalkyl | carboethoxy |
| Dehydropiperidinedione | cycloalkyl | carboxyl |
| Dehydropiperidinedione | cycloalkyl | amino |
| Dihydropyridazinone | cycloalkyl | hydroxy |
| Dihydropyridazinone | cycloalkyl | isobutylsulfonyl |
| Dihydropyridazinone | cycloalkyl | trifluoromethyl |
| Dihydropyridazinone | cycloalkyl | carboxamidobenzyl |
| Dihydropyridazinone | cycloalkyl | carboxamidobutyl-2-yl |
| Dihydropyridazinone | cycloalkyl | isobutyramido |
| Dihydropyridazinone | cycloalkyl | isobutoxy |
| Dihydropyridazinone | cycloalkyl | carboethoxy |
| Dihydropyridazinone | cycloalkyl | carboxyl |
| Dihydropyridazinone | cycloalkyl | amino |
| Dihydroisoxazinone | cycloalkyl | hydroxy |
| Dihydroisoxazinone | cycloalkyl | isobutylsulfonyl |
| Dihydroisoxazinone | cycloalkyl | trifluoromethyl |
| Dihydroisoxazinone | cycloalkyl | carboxamidobenzyl |
| Dihydroisoxazinone | cycloalkyl | carboxamidobutyl-2-yl |
| Dihydroisoxazinone | cycloalkyl | isobutyramido |
| Dihydroisoxazinone | cycloalkyl | isobutoxy |
| Dihydroisoxazinone | cycloalkyl | carboethoxy |
| Dihydroisoxazinone | cycloalkyl | carboxyl |
| Dihydroisoxazinone | cycloalkyl | amino |
| Tetrahydrotriazinedione | cycloalkyl | hydroxy |
| Tetrahydrotriazinedione | cycloalkyl | isobutylsulfonyl |
| Tetrahydrotriazinedione | cycloalkyl | trifluoromethyl |
| Tetrahydrotriazinedione | cycloalkyl | carboxamidobenzyl |
| Tetrahydrotriazinedione | cycloalkyl | carboxamidobutyl-2-yl |
| Tetrahydrotriazinedione | cycloalkyl | isobutyramido |
| Tetrahydrotriazinedione | cycloalkyl | isobutoxy |
| Tetrahydrotriazinedione | cycloalkyl | carboethoxy |
| Tetrahydrotriazinedione | cycloalkyl | carboxyl |
| Tetrahydrotriazinedione | cycloalkyl | amino |
| Tetrahydrotriazinone | cycloalkyl | hydroxy |
| Tetrahydrotriazinone | cycloalkyl | isobutylsulfonyl |
| Tetrahydrotriazinone | cycloalkyl | trifluoromethyl |
| Tetrahydrotriazinone | cycloalkyl | carboxamidobenzyl |
| Tetrahydrotriazinone | cycloalkyl | carboxamidobutyl-2-yl |
| Tetrahydrotriazinone | cycloalkyl | isobutyramido |
| Tetrahydrotriazinone | cycloalkyl | isobutoxy |
| Tetrahydrotriazinone | cycloalkyl | carboethoxy |
| Tetrahydrotriazinone | cycloalkyl | carboxyl |
| Tetrahydrotriazinone | cycloalkyl | amino |
| Piperidine | cycloalkyl | hydroxy |
| Piperidine | cycloalkyl | isobutylsulfonyl |
| Piperidine | cycloalkyl | trifluoromethyl |
| Piperidine | cycloalkyl | carboxamidobenzyl |
| Piperidine | cycloalkyl | carboxamidobutyl-2-yl |
| Piperidine | cycloalkyl | isobutyramido |
| Piperidine | cycloalkyl | isobutoxy |
| Piperidine | cycloalkyl | carboethoxy |
| Piperidine | cycloalkyl | carboxyl |
| Piperidine | cycloalkyl | amino |
| Piperazine | cycloalkyl | hydroxy |
| Piperazine | cycloalkyl | isobutylsulfonyl |
| Piperazine | cycloalkyl | trifluoromethyl |
| Piperazine | cycloalkyl | carboxamidobenzyl |
| Piperazine | cycloalkyl | carboxamidobutyl-2-yl |
| Piperazine | cycloalkyl | isobutyramido |
| Piperazine | cycloalkyl | isobutoxy |
| Piperazine | cycloalkyl | carboethoxy |
| Piperazine | cycloalkyl | carboxyl |
| Piperazine | cycloalkyl | amino |
| Piperidinone | substituted cycloalkyl | hydroxy |
| Piperidinone | substituted cycloalkyl | isobutylsulfonyl |
| Piperidinone | substituted cycloalkyl | trifluoromethyl |
| Piperidinone | substituted cycloalkyl | carboxamidobenzyl |
| Piperidinone | substituted cycloalkyl | carboxamidobutyl-2-yl |
| Piperidinone | substituted cycloalkyl | isobutyramido |
| Piperidinone | substituted cycloalkyl | isobutoxy |
| Piperidinone | substituted cycloalkyl | carboethoxy |
| Piperidinone | substituted cycloalkyl | carboxyl |
| Piperidinone | substituted cycloalkyl | amino |
| Dihydropyrimidinone | substituted cycloalkyl | hydroxy |
| Dihydropyrimidinone | substituted cycloalkyl | isobutylsulfonyl |
| Dihydropyrimidinone | substituted cycloalkyl | trifluoromethyl |
| Dihydropyrimidinone | substituted cycloalkyl | carboxamidobenzyl |
| Dihydropyrimidinone | substituted cycloalkyl | carboxamidobutyl-2-yl |
| Dihydropyrimidinone | substituted cycloalkyl | isobutyramido |
| Dihydropyrimidinone | substituted cycloalkyl | isobutoxy |
| Dihydropyrimidinone | substituted cycloalkyl | carboethoxy |
| Dihydropyrimidinone | substituted cycloalkyl | carboxyl |
| Dihydropyrimidinone | substituted cycloalkyl | amino |
| Tetrahydropyrimidinone | substituted cycloalkyl | hydroxy |
| Tetrahydropyrimidinone | substituted cycloalkyl | isobutylsulfonyl |
| Tetrahydropyrimidinone | substituted cycloalkyl | trifluoromethyl |
| Tetrahydropyrimidinone | substituted cycloalkyl | carboxamidobenzyl |
| Tetrahydropyrimidinone | substituted cycloalkyl | carboxamidobutyl-2-yl |
| Tetrahydropyrimidinone | substituted cycloalkyl | isobutyramido |
| Tetrahydropyrimidinone | substituted cycloalkyl | isobutoxy |
| Tetrahydropyrimidinone | substituted cycloalkyl | carboethoxy |
| Tetrahydropyrimidinone | substituted cycloalkyl | carboxyl |
| Tetrahydropyrimidinone | substituted cycloalkyl | amino |
| Dehydropiperidinedione | substituted cycloalkyl | hydroxy |
| Dehydropiperidinedione | substituted cycloalkyl | isobutylsulfonyl |
| Dehydropiperidinedione | substituted cycloalkyl | trifluoromethyl |
| Dehydropiperidinedione | substituted cycloalkyl | carboxamidobenzyl |
| Dehydropiperidinedione | substituted cycloalkyl | carboxamidobutyl-2-yl |
| Dehydropiperidinedione | substituted cycloalkyl | isobutyramido |
| Dehydropiperidinedione | substituted cycloalkyl | isobutoxy |
| Dehydropiperidinedione | substituted cycloalkyl | carboethoxy |
| Dehydropiperidinedione | substituted cycloalkyl | carboxyl |
| Dehydropiperidinedione | substituted cycloalkyl | amino |

TABLE 1-continued

| Core | $Z_1$ | $R_{44}$ |
|---|---|---|
| Dihydropyridazinone | substituted cycloalkyl | hydroxy |
| Dihydropyridazinone | substituted cycloalkyl | isobutylsulfonyl |
| Dihydropyridazinone | substituted cycloalkyl | trifluoromethyl |
| Dihydropyridazinone | substituted cycloalkyl | carboxamidobenzyl |
| Dihydropyridazinone | substituted cycloalkyl | carboxamidobutyl-2-yl |
| Dihydropyridazinone | substituted cycloalkyl | isobutyramido |
| Dihydropyridazinone | substituted cycloalkyl | isobutoxy |
| Dihydropyridazinone | substituted cycloalkyl | carboethoxy |
| Dihydropyridazinone | substituted cycloalkyl | carboxyl |
| Dihydropyridazinone | substituted cycloalkyl | amino |
| Dihydroisoxazinone | substituted cycloalkyl | hydroxy |
| Dihydroisoxazinone | substituted cycloalkyl | isobutylsulfonyl |
| Dihydroisoxazinone | substituted cycloalkyl | trifluoromethyl |
| Dihydroisoxazinone | substituted cycloalkyl | carboxamidobenzyl |
| Dihydroisoxazinone | substituted cycloalkyl | carboxamidobutyl-2-yl |
| Dihydroisoxazinone | substituted cycloalkyl | isobutyramido |
| Dihydroisoxazinone | substituted cycloalkyl | isobutoxy |
| Dihydroisoxazinone | substituted cycloalkyl | carboethoxy |
| Dihydroisoxazinone | substituted cycloalkyl | carboxyl |
| Dihydroisoxazinone | substituted cycloalkyl | amino |
| Tetrahydrotriazinedione | substituted cycloalkyl | hydroxy |
| Tetrahydrotriazinedione | substituted cycloalkyl | isobutylsulfonyl |
| Tetrahydrotriazinedione | substituted cycloalkyl | trifluoromethyl |
| Tetrahydrotriazinedione | substituted cycloalkyl | carboxamidobenzyl |
| Tetrahydrotriazinedione | substituted cycloalkyl | carboxamidobutyl-2-yl |
| Tetrahydrotriazinedione | substituted cycloalkyl | isobutyramido |
| Tetrahydrotriazinedione | substituted cycloalkyl | isobutoxy |
| Tetrahydrotriazinedione | substituted cycloalkyl | carboethoxy |
| Tetrahydrotriazinedione | substituted cycloalkyl | carboxyl |
| Tetrahydrotriazinedione | substituted cycloalkyl | amino |
| Tetrahydrotriazinone | substituted cycloalkyl | hydroxy |
| Tetrahydrotriazinone | substituted cycloalkyl | isobutylsulfonyl |
| Tetrahydrotriazinone | substituted cycloalkyl | trifluoromethyl |
| Tetrahydrotriazinone | substituted cycloalkyl | carboxamidobenzyl |
| Tetrahydrotriazinone | substituted cycloalkyl | carboxamidobutyl-2-yl |
| Tetrahydrotriazinone | substituted cycloalkyl | isobutyramido |
| Tetrahydrotriazinone | substituted cycloalkyl | isobutoxy |
| Tetrahydrotriazinone | substituted cycloalkyl | carboethoxy |
| Tetrahydrotriazinone | substituted cycloalkyl | carboxyl |
| Tetrahydrotriazinone | substituted cycloalkyl | amino |
| Piperidine | substituted cycloalkyl | hydroxy |
| Piperidine | substituted cycloalkyl | isobutylsulfonyl |
| Piperidine | substituted cycloalkyl | trifluoromethyl |
| Piperidine | substituted cycloalkyl | carboxamidebenzyl |
| Piperidine | substituted cycloalkyl | carboxamidebutyl-2-yl |
| Piperidine | substituted cycloalkyl | isobutyramide |
| Piperidine | substituted cycloalkyl | isobutoxy |
| Piperidine | substituted cycloalkyl | carboethoxy |
| Piperidine | substituted cycloalkyl | carboxyl |
| Piperidine | substituted cycloalkyl | amino |
| Piperazine | substituted cycloalkyl | hydroxy |
| Piperazine | substituted cycloalkyl | isobutylsulfonyl |
| Piperazine | substituted cycloalkyl | trifluoromethyl |
| Piperazine | substituted cycloalkyl | carboxamidobenzyl |
| Piperazine | substituted cycloalkyl | carboxamidobutyl-2-yl |
| Piperazine | substituted cycloalkyl | isobutyramido |
| Piperazine | substituted cycloalkyl | isobutoxy |
| Piperazine | substituted cycloalkyl | carboethoxy |
| Piperazine | substituted cycloalkyl | carboxyl |
| Piperazine | substituted cycloalkyl | amino |

In a perfect embodiment, the compounds correspound to any of Formulae A, B, C, or D and the core, $Z_1$ and $R_{44}$ are as identified in Table 2.

TABLE 2

| Core | $Z_1$ | $R_{44}$ |
|---|---|---|
| Piperidinone | methyl, ethyl, isopropyl, cyclopropyl, cyclobutyl, or phenyl | hydroxy |
| Piperidinone | methyl, ethyl, isopropyl, cyclopropyl, cyclobutyl, or phenyl | isobutylsulfonyl |
| Piperidinone | methyl, ethyl, isopropyl, cyclopropyl, cyclobutyl, or phenyl | trifluoromethyl |
| Piperidinone | methyl, ethyl, isopropyl, cyclopropyl, cyclobutyl, or phenyl | carboxamidobenzyl |
| Piperidinone | methyl, ethyl, isopropyl, cyclopropyl, cyclobutyl, or phenyl | carboxamidobutyl-2-yl |
| Piperidinone | methyl, ethyl, isopropyl, cyclopropyl, cyclobutyl, or phenyl | isobutyramido |
| Piperidinone | methyl, ethyl, isopropyl, cyclopropyl, cyclobutyl, or phenyl | carboethoxy |

TABLE 2-continued

| Core | $Z_1$ | $R_{44}$ |
|---|---|---|
| Piperidinone | methyl, ethyl, isopropyl, cyclopropyl, cyclobutyl, or phenyl | carboxyl |
| Piperidinone | methyl, ethyl, isopropyl, cyclopropyl, cyclobutyl, or phenyl | amino |
| Dihydropyrimidinone | methyl, ethyl, isopropyl, cyclopropyl, cyclobutyl, or phenyl | hydroxy |
| Dihydropyrimidinone | methyl, ethyl, isopropyl, cyclopropyl, cyclobutyl, or phenyl | isobutylsulfonyl |
| Dihydropyrimidinone | methyl, ethyl, isopropyl, cyclopropyl, cyclobutyl, or phenyl | trifluoromethyl |
| Dihydropyrimidinone | methyl, ethyl, isopropyl, cyclopropyl, cyclobutyl, or phenyl | carboxamidobenzyl |
| Dihydropyrimidinone | methyl, ethyl, isopropyl, cyclopropyl, cyclobutyl, or phenyl | carboxamidobutyl-2-yl |
| Dihydropyrimidinone | methyl, ethyl, isopropyl, cyclopropyl, cyclobutyl, or phenyl | isobutyramido |
| Dihydropyrimidinone | methyl, ethyl, isopropyl, cyclopropyl, cyclobutyl, or phenyl | isobutoxy |
| Dihydropyrimidinone | methyl, ethyl, isopropyl, cyclopropyl, cyclobutyl, or phenyl | carboethoxy |
| Dihydropyrimidinone | methyl, ethyl, isopropyl, cyclopropyl, cyclobutyl, or phenyl | carboxyl |
| Dihydropyrimidinone | methyl, ethyl, isopropyl, cyclopropyl, cyclobutyl, or phenyl | amino |
| Tetrahydropyrimidinone | methyl, ethyl, isopropyl, cyclopropyl, cyclobutyl, or phenyl | hydroxy |
| Tetrahydropyrimidinone | methyl, ethyl, isopropyl, cyclopropyl, cyclobutyl, or phenyl | isobutylsulfonyl |
| Tetrahydropyrimidinone | methyl, ethyl, isopropyl, cyclopropyl, cyclobutyl, or phenyl | trifluoromethyl |
| Tetrahydropyrimidinone | methyl, ethyl, isopropyl, cyclopropyl, cyclobutyl, or phenyl | carboxamidobenzyl |
| Tetrahydropyrimidinone | methyl, ethyl, isopropyl, cyclopropyl, cyclobutyl, or phenyl | carboxamidobutyl-2-yl |
| Tetrahydropyrimidinone | methyl, ethyl, isopropyl, cyclopropyl, cyclobutyl, or phenyl | isobutyramido |
| Tetrahydropyrimidinone | methyl, ethyl, isopropyl, cyclopropyl, cyclobutyl, or phenyl | isobutoxy |
| Tetrahydropyrimidinone | methyl, ethyl, isopropyl, cyclopropyl, cyclobutyl, or phenyl | carboethoxy |
| Tetrahydropyrimidinone | methyl, ethyl, isopropyl, cyclopropyl, cyclobutyl, or phenyl | carboxyl |
| Tetrahydropyrimidinone | methyl, ethyl, isopropyl, cyclopropyl, cyclobutyl, or phenyl | amino |
| Dehydropiperidinedione | methyl, ethyl, isopropyl, cyclopropyl, cyclobutyl, or phenyl | hydroxy |
| Dehydropiperidinedione | methyl, ethyl, isopropyl, cyclopropyl, cyclobutyl, or phenyl | isobutylsulfonyl |
| Dehydropiperidinedione | methyl, ethyl, isopropyl, cyclopropyl, cyclobutyl, or phenyl | trifluoromethyl |
| Dehydropiperidinedione | methyl, ethyl, isopropyl, cyclopropyl, cyclobutyl, or phenyl | carboxamidobenzyl |
| Dehydropiperidinedione | methyl, ethyl, isopropyl, cyclopropyl, cyclobutyl, or phenyl | carboxamidobutyl-2-yl |
| Dehydropiperidinedione | methyl, ethyl, isopropyl, cyclopropyl, cyclobutyl, or phenyl | isobutyramido |
| Dehydropiperidinedione | methyl, ethyl, isopropyl, cyclopropyl, cyclobutyl, or phenyl | isobutoxy |
| Dehydropiperidinedione | methyl, ethyl, isopropyl, cyclopropyl, cyclobutyl, or phenyl | carboethoxy |
| Dehydropiperidinedione | methyl, ethyl, isopropyl, cyclopropyl, cyclobutyl, or phenyl | carboxyl |
| Dehydropiperidinedione | methyl, ethyl, isopropyl, cyclopropyl, cyclobutyl, or phenyl | amino |
| Dihydropyridazinone | methyl, ethyl, isopropyl, cyclopropyl, cyclobutyl, or phenyl | hydroxy |
| Dihydropyridazinone | methyl, ethyl, isopropyl, cyclopropyl, cyclobutyl, or phenyl | isobutylsulfonyl |
| Dihydropyridazinone | methyl, ethyl, isopropyl, cyclopropyl, cyclobutyl, or phenyl | trifluoromethyl |
| Dihydropyridazinone | methyl, ethyl, isopropyl, cyclopropyl, cyclobutyl, or phenyl | carboxamidobenzyl |
| Dihydropyridazinone | methyl, ethyl, isopropyl, cyclopropyl, cyclobutyl, or phenyl | carboxamidobutyl-2-yl |
| Dihydropyridazinone | methyl, ethyl, isopropyl, cyclopropyl, cyclobutyl, or phenyl | isobutyramido |
| Dihydropyridazinone | methyl, ethyl, isopropyl, cyclopropyl, cyclobutyl, or phenyl | isobutoxy |
| Dihydropyridazinone | methyl, ethyl, isopropyl, cyclopropyl, cyclobutyl, or phenyl | carboethoxy |
| Dihydropyridazinone | methyl, ethyl, isopropyl, cyclopropyl, cyclobutyl, or phenyl | carboxyl |
| Dihydropyridazinone | methyl, ethyl, isopropyl, cyclopropyl, cyclobutyl, or phenyl | amino |
| Dihydroisoxazinone | methyl, ethyl, isopropyl, cyclopropyl, cyclobutyl, or phenyl | hydroxy |
| Dihydroisoxazinone | methyl, ethyl, isopropyl, cyclopropyl, cyclobutyl, or phenyl | isobutylsulfonyl |
| Dihydroisoxazinone | methyl, ethyl, isopropyl, cyclopropyl, cyclobutyl, or phenyl | trifluoromethyl |
| Dihydroisoxazinone | methyl, ethyl, isopropyl, cyclopropyl, cyclobutyl, or phenyl | carboxamidobenzyl |
| Dihydroisoxazinone | methyl, ethyl, isopropyl, cyclopropyl, cyclobutyl, or phenyl | carboxamidobutyl-2-yl |
| Dihydroisoxazinone | methyl, ethyl, isopropyl, cyclopropyl, cyclobutyl, or phenyl | isobutyramido |
| Dihydroisoxazinone | methyl, ethyl, isopropyl, cyclopropyl, cyclobutyl, or phenyl | isobutoxy |
| Dihydroisoxazinone | methyl, ethyl, isopropyl, cyclopropyl, cyclobutyl, or phenyl | carboethoxy |

TABLE 2-continued

| Core | $Z_1$ | $R_{44}$ |
|---|---|---|
| Dihydro-isoxazinone | methyl, ethyl, isopropyl, cyclopropyl, cyclobutyl, or phenyl | carboxyl |
| Dihydro-isoxazinone | methyl, ethyl, isopropyl, cyclopropyl, cyclobutyl, or phenyl | amino |
| Tetrahydro-triazinedione | methyl, ethyl, isopropyl, cyclopropyl, cyclobutyl, or phenyl | hydroxy |
| Tetrahydro-triazinedione | methyl, ethyl, isopropyl, cyclopropyl, cyclobutyl, or phenyl | isobutylsulfonyl |
| Tetrahydro-triazinedione | methyl, ethyl, isopropyl, cyclopropyl, cyclobutyl, or phenyl | trifluoromethyl |
| Tetrahydro-triazinedione | methyl, ethyl, isopropyl, cyclopropyl, cyclobutyl, or phenyl | carboxamidobenzyl |
| Tetrahydro-triazinedione | methyl, ethyl, isopropyl, cyclopropyl, cyclobutyl, or phenyl | carboxamidobutyl-2-yl |
| Tetrahydro-triazinedione | methyl, ethyl, isopropyl, cyclopropyl, cyclobutyl, or phenyl | isobutyramido |
| Tetrahydro-triazinedione | methyl, ethyl, isopropyl, cyclopropyl, cyclobutyl, or phenyl | isobutoxy |
| Tetrahydro-triazinedione | methyl, ethyl, isopropyl, cyclopropyl, cyclobutyl, or phenyl | carboethoxy |
| Tetrahydro-triazinedione | methyl, ethyl, isopropyl, cyclopropyl, cyclobutyl, or phenyl | carboxyl |
| Tetrahydro-triazinedione | methyl, ethyl, isopropyl, cyclopropyl, cyclobutyl, or phenyl | amino |
| Tetrahydro-triazinone | methyl, ethyl, isopropyl, cyclopropyl, cyclobutyl, or phenyl | hydroxy |
| Tetrahydro-triazinone | methyl, ethyl, isopropyl, cyclopropyl, cyclobutyl, or phenyl | isobutylsulfonyl |
| Tetrahydro-triazinone | methyl, ethyl, isopropyl, cyclopropyl, cyclobutyl, or phenyl | trifluoromethyl |
| Tetrahydro-triazinone | methyl, ethyl, isopropyl, cyclopropyl, cyclobutyl, or phenyl | carboxamidobenzyl |
| Tetrahydro-triazinone | methyl, ethyl, isopropyl, cyclopropyl, cyclobutyl, or phenyl | carboxamidobutyl-2-yl |
| Tetrahydro-triazinone | methyl, ethyl, isopropyl, cyclopropyl, cyclobutyl, or phenyl | isobutyramido |
| Tetrahydro-triazinone | methyl, ethyl, isopropyl, cyclopropyl, cyclobutyl, or phenyl | isobutoxy |
| Tetrahydro-triazinone | methyl, ethyl, isopropyl, cyclopropyl, cyclobutyl, or phenyl | carboethoxy |
| Tetrahydro-triazinone | methyl, ethyl, isopropyl, cyclopropyl, cyclobutyl, or phenyl | carboxyl |
| Tetrahydro-triazinone | methyl, ethyl, isopropyl, cyclopropyl, cyclobutyl, or phenyl | amino |
| Piperidine | methyl, ethyl, isopropyl, cyclopropyl, cyclobutyl, or phenyl | hydroxy |
| Piperidine | methyl, ethyl, isopropyl, cyclopropyl, cyclobutyl, or phenyl | isobutylsulfonyl |
| Piperidine | methyl, ethyl, isopropyl, cyclopropyl, cyclobutyl, or phenyl | trifluoromethyl |
| Piperidine | methyl, ethyl, isopropyl, cyclopropyl, cyclobutyl, or phenyl | carboxamidobenzyl |
| Piperidine | methyl, ethyl, isopropyl, cyclopropyl, cyclobutyl, or phenyl | carboxamidobutyl-2-yl |
| Piperidine | methyl, ethyl, isopropyl, cyclopropyl, cyclobutyl, or phenyl | isobutyramido |
| Piperidine | methyl, ethyl, isopropyl, cyclopropyl, cyclobutyl, or phenyl | isobutoxy |
| Piperidine | methyl, ethyl, isopropyl, cyclopropyl, cyclobutyl, or phenyl | carboethoxy |
| Piperidine | methyl, ethyl, isopropyl, cyclopropyl, cyclobutyl, or phenyl | carboxyl |
| Piperidine | methyl, ethyl, isopropyl, cyclopropyl, cyclobutyl, or phenyl | amino |
| Piperazine | methyl, ethyl, isopropyl, cyclopropyl, cyclobutyl, or phenyl | hydroxy |
| Piperazine | methyl, ethyl, isopropyl, cyclopropyl, cyclobutyl, or phenyl | isobutylsulfonyl |
| Piperazine | methyl, ethyl, isopropyl, cyclopropyl, cyclobutyl, or phenyl | trifluoromethyl |
| Piperazine | methyl, ethyl, isopropyl, cyclopropyl, cyclobutyl, or phenyl | carboxamidobenzyl |
| Piperazine | methyl, ethyl, isopropyl, cyclopropyl, cyclobutyl, or phenyl | carboxamidobutyl-2-yl |
| Piperazine | methyl, ethyl, isopropyl, cyclopropyl, cyclobutyl, or phenyl | isobutyramido |
| Piperazine | methyl, ethyl, isopropyl, cyclopropyl, cyclobutyl, or phenyl | isobutoxy |
| Piperazine | methyl, ethyl, isopropyl, cyclopropyl, cyclobutyl, or phenyl | carboethoxy |
| Piperazine | methyl, ethyl, isopropyl, cyclopropyl, cyclobutyl, or phenyl | carboxyl |
| Piperazine | methyl, ethyl, isopropyl, cyclopropyl, cyclobutyl, or phenyl | amino |

For convenience, each of the core heterocyclic rings and $R_{44}$ moieties identified in Tables 1 and 2 are set forth below.

Heterocyclic Core Ring Structures

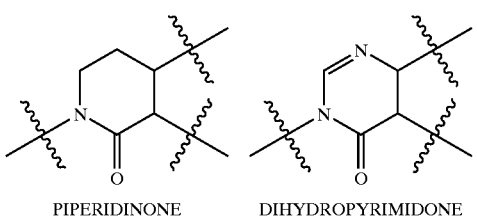

PIPERIDINONE     DIHYDROPYRIMIDONE

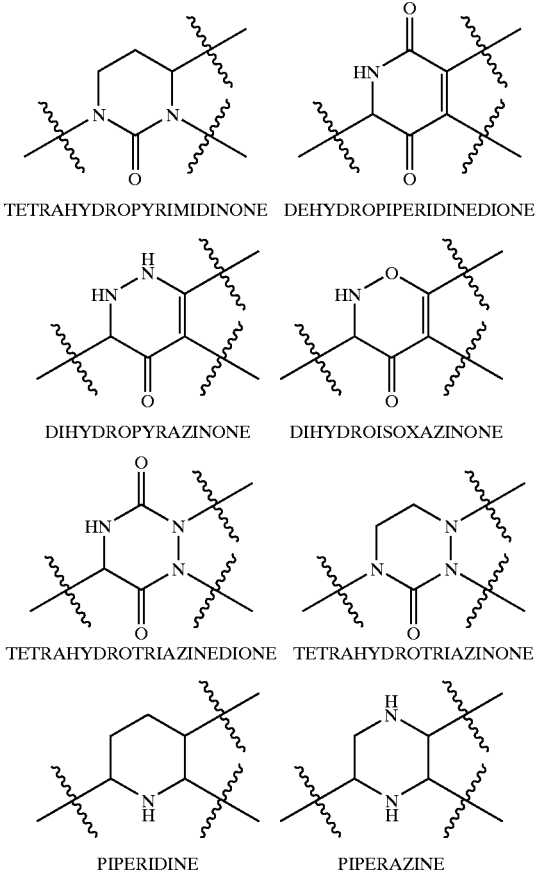
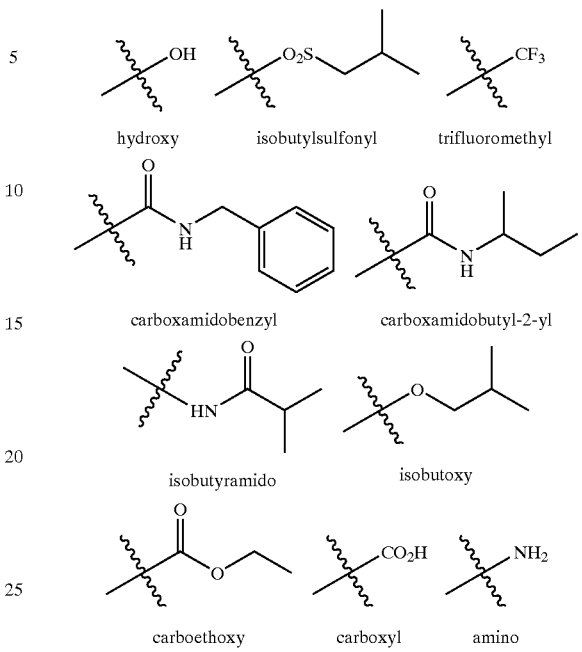
R44 Moieties
In another preferred embodiment, the compounds corresponding to either of formulas (1) and (2) are selected from the group of compounds illustrated in Table 3 below wherein for any given compound, $Z_1$ is isopropyl, cyclopropyl, cyclobutyl, trifluoroethyl, or carboxymethyl.
TABLE 3
| Compound No. | Compound |
|---|---|
| 1 | 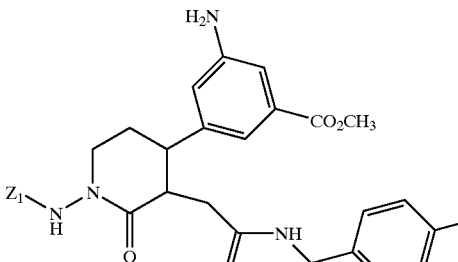 |
| 2 | 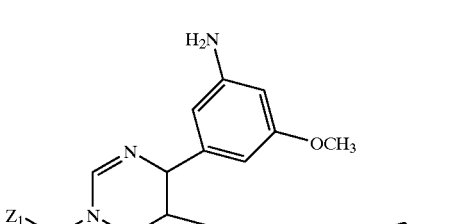 |

TABLE 3-continued
| Compound No. | Compound |
|---|---|
| 3 | 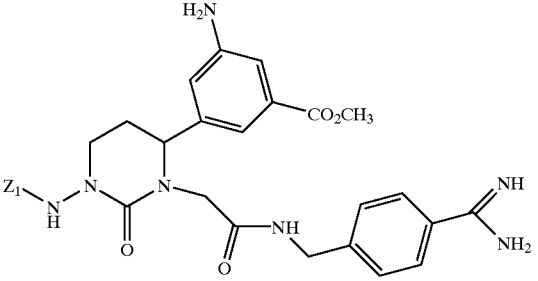 |
| 4 | 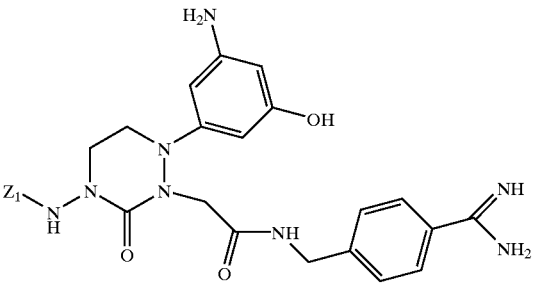 |
| 5 | 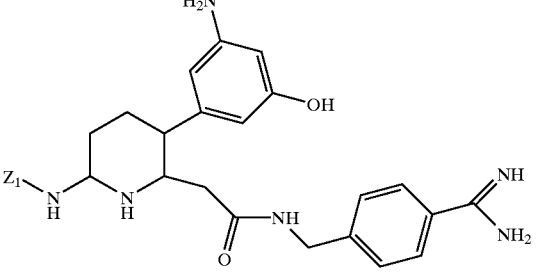 |
| 6 | 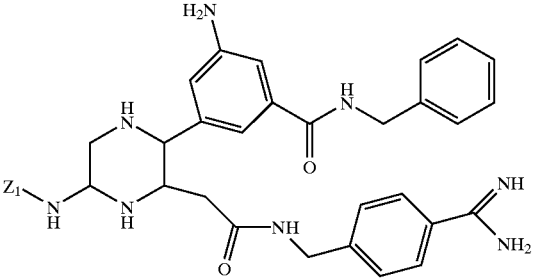 |
| 7 | 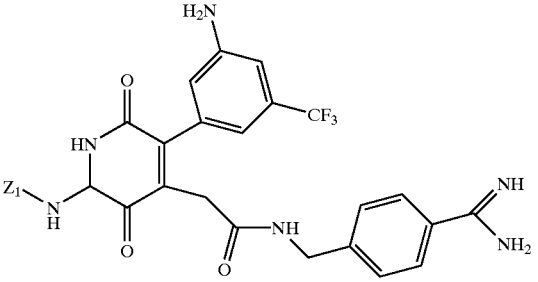 |

TABLE 3-continued

| Compound No. | Compound |
|---|---|
| 8 | (structure: triazine-dione core with $Z_1$-NH substituent, N-aryl group bearing $CF_3$ and $H_2N$, linked via $CH_2C(O)NH$-benzyl-amidine) |
| 9 | (structure: oxazine ring with $Z_1$-NH, aryl bearing $H_2N$ and $SO_2Bu$, linked via $CH_2C(O)NH$-benzyl-amidine) |
| 10 | (structure: pyridazinone with $Z_1$-NH, aryl bearing $H_2N$ and $CO_2H$, linked via $CH_2C(O)NH$-benzyl-amidine) |

Any prodrug compound of the present invention having one or more prodrug moieties as part of the molecule, can be converted under physiological conditions to the biologically active drug by a number of chemical and biological mechanisms. In general terms, as detailed above, these prodrug conversion mechanisms are hydrolysis, reduction, oxidation, and elimination. For illustrative purposes, the following paragraphs detail prodrugs in which the prodrug moiety is covalently bonded to the amidine group on $Z_3$.

In one embodiment, conversion of the prodrug to the biologically active drug can be accomplished by hydrolysis of the prodrug moiety provided the prodrug moiety is chemically or enzymatically hydrolyzable with water. The reaction with water typically results in removal of the prodrug moiety and liberation of the biologically active drug. By way of example, a hydrolyzable prodrug derivative at the amidine group may be a carbonyl derivative such as N-acyl. Hydrolysis results in freeing the amidine group of the drug by removal of the acyl as carbon acid. Other suitable hydrolyzable prodrug derivatives include carbonyl, thiocarbonyl, imine, enamine, and oxygenated sulfur.

Yet another aspect of the invention provides conversion of the prodrug to the biologically active drug by reduction of the prodrug moiety. Typically in this embodiment, the prodrug moiety is reducible under physiological conditions in the presence of a reducing enzymatic process. The reduction preferably results in removal of the prodrug moiety and liberation of the biologically active drug. An example of a reducible prodrug derivative at the amidine group is an oxygen containing group in which an oxygen is directly attached to the amidine. Reduction results in freeing the amidine group of the drug by removal of oxygen as water or an alcohol. Generally speaking, other suitable reducible prodrug derivatives include a nitrogen containing group, and a sulfur containing group, provided both nitrogen and sulfur are each preferably in their most reduced state.

In another aspect of the invention, conversion of the prodrug to the biologically active drug can also be accomplished by oxidation of the prodrug moiety. Typically in this embodiment, the prodrug moiety is oxidizable under physiological conditions in the presence of an oxidative enzymatic process. The oxidation preferably results in removal of the prodrug moiety and liberation of the biologically active drug. An example of an oxidizable prodrug derivative at the amidine group is a hydrocarbyl containing unsaturation in the carbon beta to the carbon directly connected to the amidine group. Oxidation results in forming an oxygenated intermediate that breaks down, thereby freeing the amidine group of the drug with concurrent hydrolysis of the oxygenated hydrocarbyl residue. Other suitable oxidizable prodrug derivatives of the amidine include saturated hydrocarbyl, unsaturated substituted hydrocarbyl, aryl, and aralkyl.

A further aspect of the invention encompasses conversion of the prodrug to the biologically active drug by elimination of the prodrug moiety. Generally speaking, in this embodiment the prodrug moiety is removed under physiological conditions with a chemical or biological reaction. The elimination results in removal of the prodrug moiety and liberation of the biologically active drug. By way of example, an elimineateable prodrug derivative at the amidine group is a hydrocarbyl containing an unsaturated electron withdrawing group bonded to the carbon beta to the carbon directly connected to the amidine. More specifically, for illustration purposes and exemplification, the hydrocarbyl group could have a cyano group beta to the carbon directly bonded to the amidino group. Elimination results in the freeing of the amidine group of the drug with concurrent removal of the unsaturated hydrocarbyl residue derived from the prodrug moiety. Other suitable elimineateable prodrug derivatives of the amidine include a hydrocarbyl substituted at the beta carbon with carbonyl, alkoxycarbonyl, amidocarbonyl, nitro, or sulfonyl or an alkyl group substituted with oxygen, nitrogen or sulfur at the carbon directly bonded to the amidine group.

Any prodrug compound of the present invention may undergo any combination of the above detailed mechanisms to convert the prodrug to the biologically active compound. For example, a particular compound may undergo hydrolysis, oxidation, elimination, and reduction to convert the prodrug to the biologically active compound. Equally, a particular compound may undergo only one of these mechanisms to convert the prodrug to the biologically active compound.

As a further embodiment, compounds of the present invention or a pharmaceutically-acceptable salt thereof, comprise a treatment and prophylaxis for thrombotic events resulting from coronary artery disease, cerebrovascular disease and other coagulation cascade related disorders in a subject, comprising administering to the subject having such disorder a therapeutically-effective amount of compounds of the present invention or a pharmaceutically-acceptable salt thereof.

In another aspect of the invention, the compounds may also be used whenever inhibition of blood coagulation is required such as to prevent coagulation of stored whole blood and to prevent coagulation in other biological samples for testing or storage. Thus coagulation inhibitors of the present inhibition can be added to or contacted with stored whole blood and any medium containing or suspected of containing plasma coagulation factors and in which it is desired that blood coagulation be inhibited, e.g. when contacting the mammal's blood with material selected from the group consisting of vascular grafts, stents, orthopedic prothesis, cardiac prosthesis, and extracorporeal circulation systems.

Compounds of the invention are capable of inhibiting activity of serine proteases related to the coagulation cascade, and thus could be used in the manufacture of a medicament, a method for the prophylactic or therapeutic treatment of diseases mediated by coagulation cascade serine proteases, such as inhibiting the formation of blood platelet aggregates, inhibiting the formation of fibrin, inhibiting thrombus formation, and inhibiting embolus formation in a mammal, in blood, in blood products, and in mammalian organs. The compounds also can be used for treating or preventing unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels in a mammal. The compounds also can be used to study the mechanism of action of coagulation cascade serine proteases to enable the design of better inhibitors and development of better assay methods. The compounds would be also useful in prevention of cerebral vascular accident (CVA) or stroke.

Also included in the family of compounds are the pharmaceutically-acceptable salts thereof. The term "pharmaceutically-acceptable salt" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of formulas (1), (2), or (3) may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of formulas (1), (2), or (3) include metallic salts made from aluminum, calcium, lithium, magnesium, potassium, sodium and zinc or organic salts made from N,N'-dibenzylethyleneldiamine, choline, chloroprocaine, diethanolamine, ethylenediamine, meglumine (N-methylglucamine) and procain. All of these salts may be prepared by conventional means from the corresponding compound by reacting, for example, the appropriate acid or base with the compound of the present invention.

The present invention also comprises a pharmaceutical composition comprising a therapeutically-effective amount of the compound in association with at least one pharmaceutically-acceptable carrier, adjuvant or diluent. Pharmaceutical compositions of the present invention can comprise the active compounds in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended.

The active compounds and composition may, for example, be administered orally, intravascularly, intraperitoneally, subcutaneously, intramuscularly, oculary, or topically. For treating ocular build up of fibrin, the compounds may be administered intraocularly or topically as well as orally or parenterally.

The compounds can be administered in the form of a depot injection or implant preparation which may be formulated in such a manner as to permit a sustained release of the active ingredient. The active ingredient can be compressed into pellets or small cylinders and implanted subcutaneously or intramusculary as depot injections or implants. Implants may employ inert materials such as biodegradable polymers or synthetic silicones, for example, Silastic, silicone rubber or other silicon containing polymers.

The compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or ployethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphitpathic block copolymers of hydrogels.

For oral administration, the pharmaceutical composition may be in the form of, for example, tablets, capsules (each of which includes sustained release or timed release formulations), pills, powders, granules, elixers, tinctures, suspensions, liquids including syrups, and emulsions. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of the present invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

In practicing the methods of the present invention for the treatment and prevention of a variety of thrombotic conditions resulting from coronary artery and cerebrovascular disease, the compounds and pharmaceutical compositions of the present invention are administered alone or in combination with one another, or in combination with other therapeutics or in vivo diagnostic agents. The coagulation cascade inhibitors of the present invention can also be co-administered with suitable anti-platelet aggregation agents, including, but not limited to ticlopidine, clopidrogel, or aspirin, fibrinogen receptor antagonists (e.g., to treat or prevent unstable angina or to prevent reocculsion after angioplasty and restenosis), anti-coagulants such as warfarin or heparins, thrombolytic agents such as plasminogen activators or streptokinase to achieve synergistic effects in the treatment of various pathologies, lipid lowering agents including antihypercholesterolemics (e.g., HMG CoA reductase inhibitors such as mevastatin, lovastatin, simvastatin, pravastatin, and fluvastatin, HMG CoA synthatase inhibitors, etc.), anti-diabetic drugs, or other cardiovascular agents (loop diuretics, thiazide type diuretics, nitrates, aldosterone antagonistics (i.e., spironolactone and eplerenone), angiotensin converting enzyme (ACE) inhibitors, angiotensin II receptor antagonists, beta-blockers, antiarrythmics, anti-hypertension agents, and calcium channel blockers) to treat or prevent atheriosclerosis. For example, patients suffering from coronary artery disease, and patients subjected to angioplasty procedures, would benefit from coadministration of fibrinogen receptor antagonists and coagulation cascade inhibitors of the present invention. Also, coagulation cascade inhibitors could enhance the efficiency of tissue plasminogen activator-mediated thrombolytic reperfusion.

Typical doses of coagulation cascade inhibitors of the present invention with other suitable anti-platelet agents, anticoagulation agents, cardiovascular therapeutic agents, or thrombolytic agents may be the same as those doses of coagulation cascade inhibitors administered without coadministration of additional anti-platelet agents, anticoagulation agents, cardiovascular therapeutic agents, or thrombolytic agents, or may be substantially less than those doses of coagulation cascade inhibitors administered without coadministration of additional anti-platelet agents, anticoagulation agents, cardiovascular therapeutic agents, or thrombolytic agents, depending on a patient's therapeutic needs.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention. Pharmaceutically acceptable salts of such tautomeric, geometric or stereoisomeric forms are also included within the invention.

The terms "cis" and "trans", as used herein, denote a form of geometric isomerism in which two carbon atoms connected by a double bond will each have a hydrogen atom on the same side of the double bond ("sis") or on opposite sides of the double bond ("trans").

Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

The present novel methods preferably employ compounds which selectively inhibit human TF-VIIa over the inhibition of both human Thrombin II and human factor Xa. Preferably, the compounds have a human TF-VIIa $IC_{50}$ of less than 0.5 uM and also have a selectivity ratio of TF-VIIa inhibition over both human Thrombin II and human factor Xa inhibition of at least 10, and more preferably at least 100. Even more preferably, the compounds have a human TF-VIIa $IC_{50}$ of less than 0.1 uM and also have a selectivity ratio of TF-VIIa inhibition over both human Thrombin II and human factor Xa inhibition of at least 300, more preferably at least 1000, and most preferably at least 10,000.

All mentioned references are incorporated by reference as if here written.

Although this invention has been described with respect to specific embodiments, the details of these embodiments are not to be construed as limitations. Without further elaboration, it is believed that one skilled in the art can, using the preceding descriptions, utilize the present invention to its fullest extent. Compounds containing multiple variations of the structural modifications illustrated in the Schemes are also contemplated. Those skilled in the art will readily understand that known variations of the conditions and processes of the following preparative procedures can be used to prepare these compounds.

GENERAL SYNTHETIC PROCEDURES AND SPECIFIC EXAMPLES

The compounds of the present invention can be synthesized, for example, according to the following procedures and Schemes given below.

Abbreviations used in the schemes and tables include: "AA" represents amino acids, "AcCN" represents acetonitrile, "AcOH" represents acetic acid, "BINAP" represents 2,2'-bis(diphenylphosphino)-1,1'-binaphthyl, "BnOH" represents benzyl alcohol, "BnCHO" represents 2-phenylethanal, "BnSO$_2$Cl" represents benzylsulfonyl chloride, "Boc" represents tert-butyloxycarbonyl, "BOP" represents benzotriazol-1-yl-oxy-tris-(dimethylamino), "bu" represents butyl, "dba" represents dibenzylidene-acetone, "DCC" represents 1,3-dicyclohexylcarbodiimide, "DCM" represents dichloromethane or methylene chloride, "DIBAH" or "DIBAL" represents diisobutylaluminum hydride, "DMF" represents dimethylformamide, "DMSO" represents dimethylsulfoxide, "DPPA" represents diphenylphosphoryl azide", "EDC" represents 1-[3-(dimethylamino)propyl]-3-ethylcarbodiimide hydrochloride, "Ex. No." represents Example Number, "Fmoc" represents 9-fluorenylmethoxycarbonyl, "HOBt" represents hydroxybenzoltriazole", "LDA" represents lithium diisopropylamide, "MW" represents molecular weight, "NMM" represents N-methylmorpholine, "Ph" represents phenyl or aryl, "PHTH" represents a phthaloyl group, "pnZ" represents 4-nitrobenzyloxy-carbonyl, "PTC" represents a phase transfer catalyst, "py" represents pyridine, "RNH$_2$" represents a primary organic amine, "SEM" represents 2-(trimethylsilyl)ethoxy-methyl chloride, "p-TsOH" represents paratoluenesulfonic acid, "TBAF" represents tetrabutylammonium fluoride, "TBTU" represents 2-(1H-benzotriozole-1-yl)-1,1,3,3-tetramethyluronium tetrafluoroborate, "TEA" represents triethylamine, "TFA" represents trifluoroacetic acid, "THF" represents tetrahydrofuran, "TMS" represents trimethylsilyl, "TMSCN" represents trimethylsilyl cyanide, and "Cbz" or "Z" represents benzyloxycarbonyl.

A specific synthetic process, useful in the preparation of many of the heterocyclic compounds of the present invention, is the arylation or heteroarylation of an intermediate compound characterized by having a suitable leaving group on a sp$^2$ hybridized carbon of a heterocyclic ring or a cycloalkenyl ring. In the product of the reaction, the leaving group is replaced by an aryl group or a heteroaryl group. Suitable leaving groups for the reaction include chloro, bromo, iodo, methylthio, and triflates. The heterocyclic ring or the cycloalkenyl ring with the leaving group will preferably have an acetic acid group or a derivative thereof bonded to a ring atom alpha to the bromo and a substituted or unsubstituted amino group bonded to a ring atom that is both beta to the carbon having the acetic acid group and gamma to the bromo substituted ring carbon. The aryl group that is reacted at the $sp^2$ hybridized carbon is generally an aryl boronic acid or an ester of the aryl boronic acid; similarly, heteroaryl boronic acids or esters of these boronic acids can be used in the same manner as aryl boronates. The aryl and heteroaryl boronates may be substituted or unsubstituted. The aryl or heteroaryl becomes bonded to the $sp^2$ hybridized carbon at the point at which the boron was attached to the aryl or heteroaryl ring. Aryl and heteroaryl organoSn compounds can also be used instead of the corresponding boronates.

Suitable reaction conditions for carrying out this transformation include:

1. $Pd[P(phenyl)_3]_4$, 2M $Na_2CO_3$, 60–75° C., dimethoxyethane (DME), $H_2O$, $N_2$;
2. $Pd[P(phenyl)_3]_4$, $Cs_2CO_3$, dioxane, 100° C.;
3. $Pd[P(phenyl)_3]_4$ Cu(I)-2-thiophenecarboxylate, 70–75° C., anhydrous THF, argon;
4. $Z4\text{-}Sn(n\text{-}butyl)_3$], $Pd[P(phenyl)_3]_4$, LiCl, anhydrous dioxane, 85° C., argon or $N_2$.

The organo palladium (Pd[P(phenyl)3]4) compound is used catalytically in a ratio of 1 to 40 mole %. The carbonate base is normally used in an excess of 1.2 to 2 molar equivalents. Suitable solvents include dimethoxyethane (DME), dioxane, 1-propanol, and tetrahydrofuran. The temperature of the reaction is normally in the range of from about 50 to 100° C. Cu(I)-2-thiophenecarboxylate (Cu(I)-TC) is normally used in a mole % of 110–150.

Schemes 2, 4, 5 and 6 show specific applications of this specific synthetic process. Procedures for preparing the intermediate heterocyclic or cycloalkenyl ring compounds having a suitable leaving group on $sp^2$ hybridized carbon and useful as suitable intermediates in this specific synthetic process are given in the schemes and examples listed above.

As used in the schemes and examples, $L_3$, $Z_1$, $Z_3$, $Z_4$, and $R_{44}$, along with any other variable depicted, encompass each group described for each particular variable for each embodiment of compounds having any of the formulas detailed herein. Further, $Z_5$ and $Z_6$ are independently hydrogen or halogen, $R_{4a}$ and $R_{4b}$ are hydrogen, and $L_6$ is a bond.

Scheme 1: Piperazine

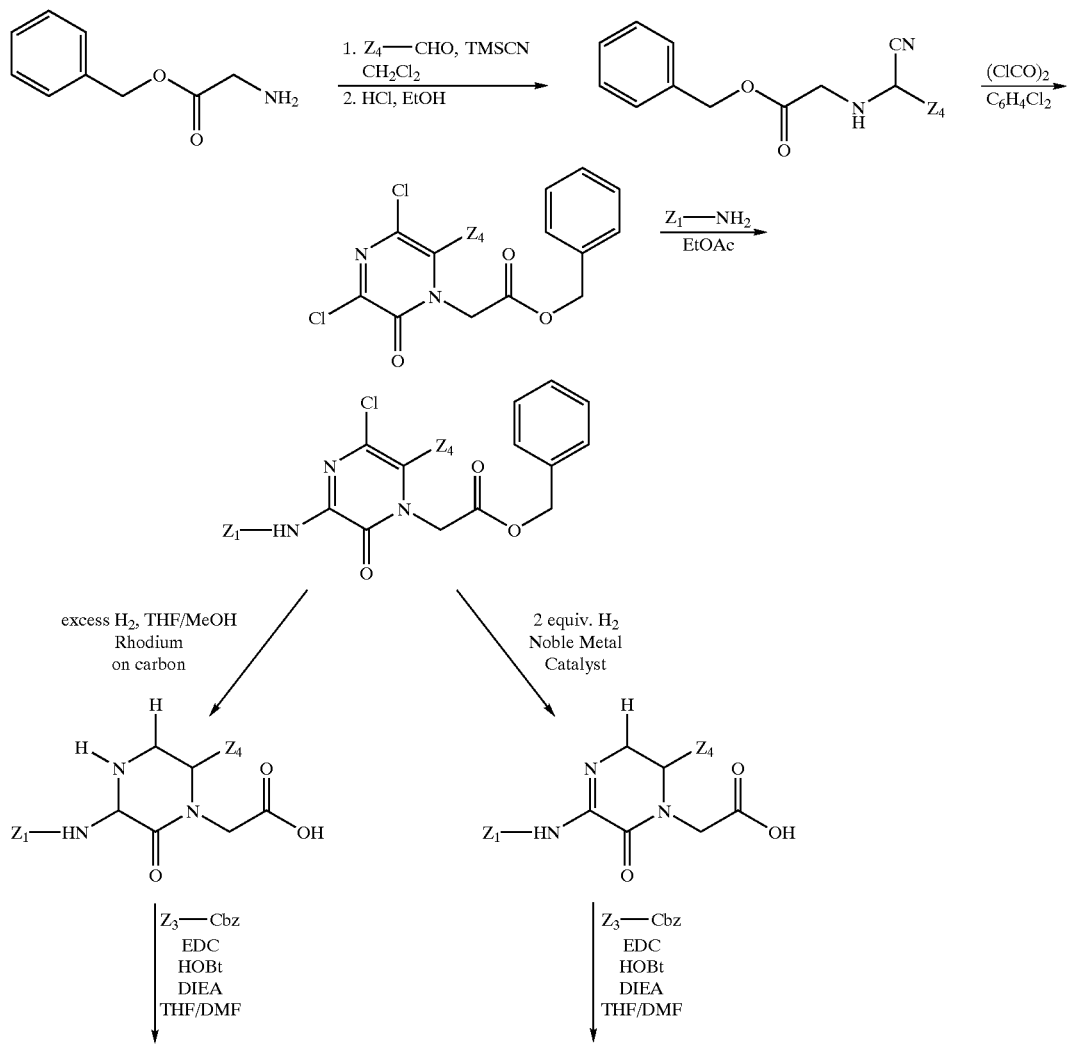

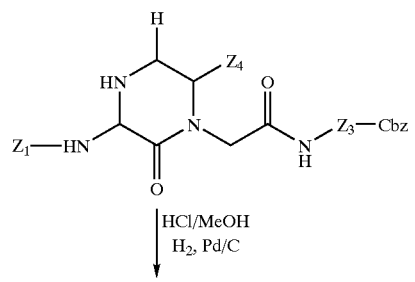
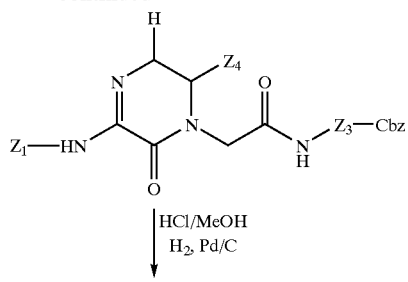
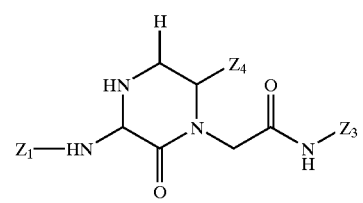
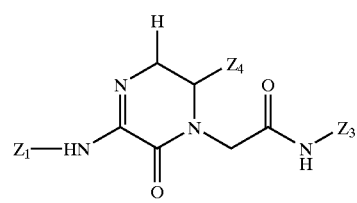
Scheme 2: Piperidine
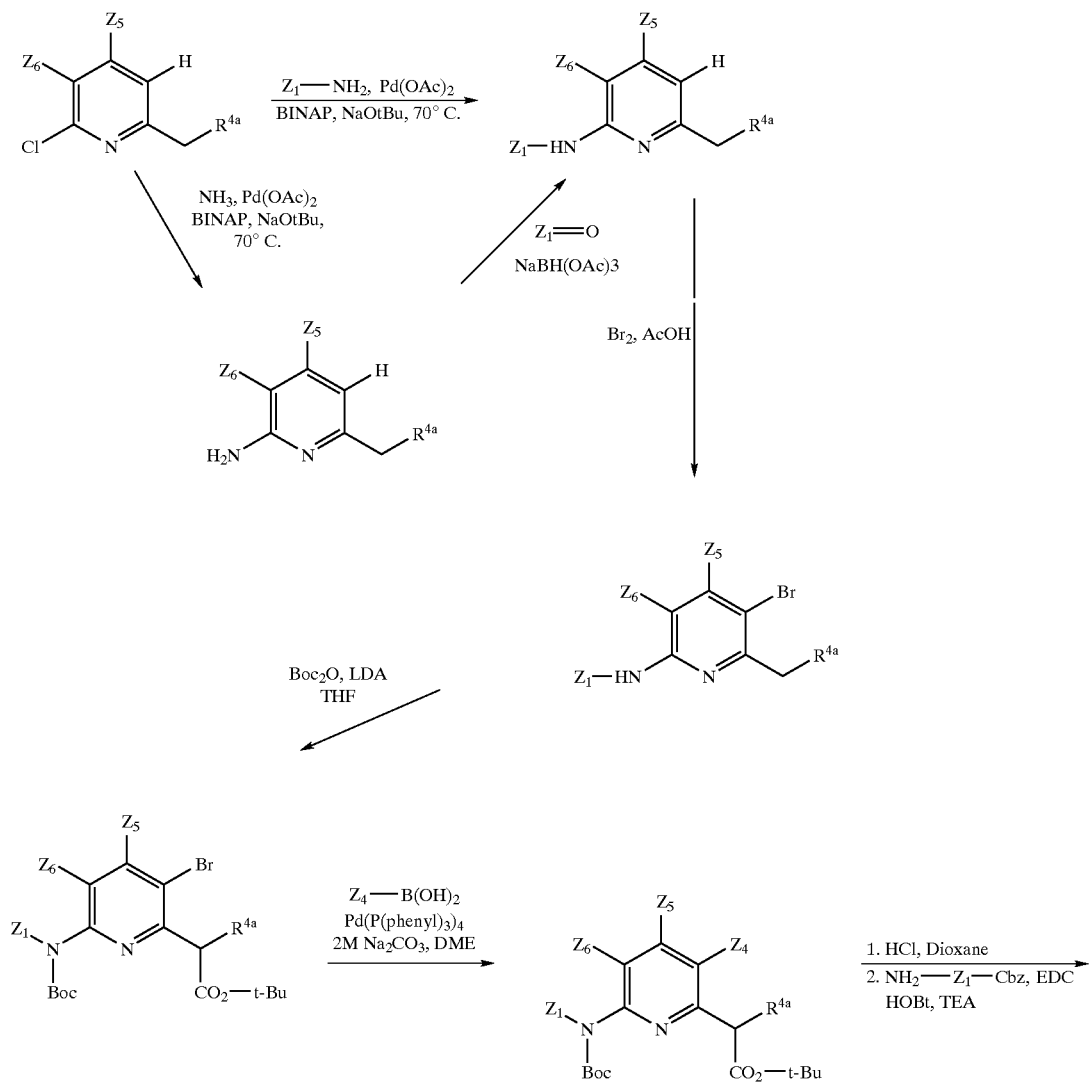

-continued
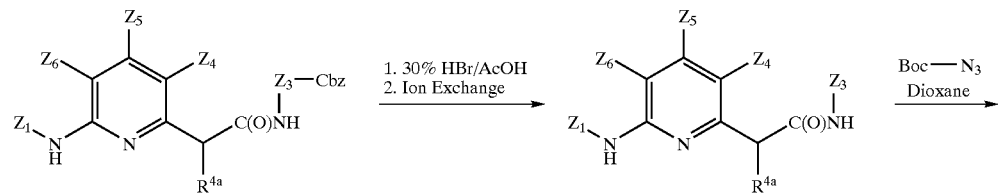
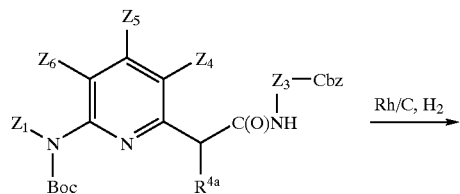
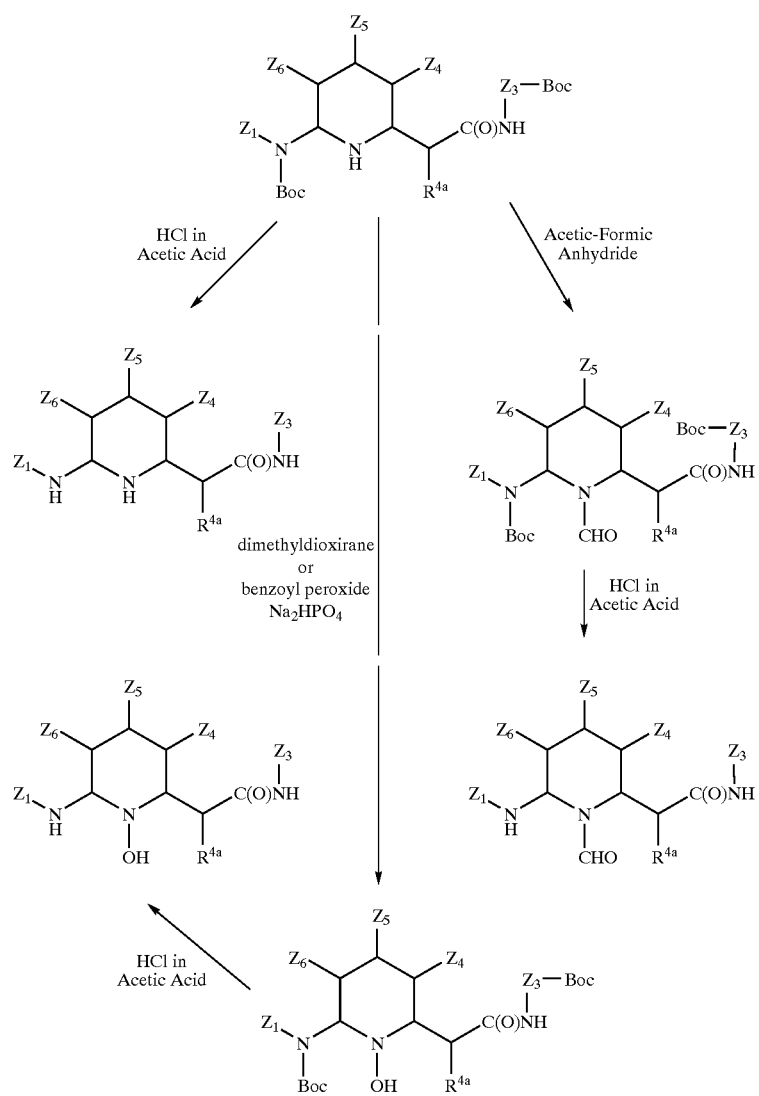

Scheme 3: Piperidone
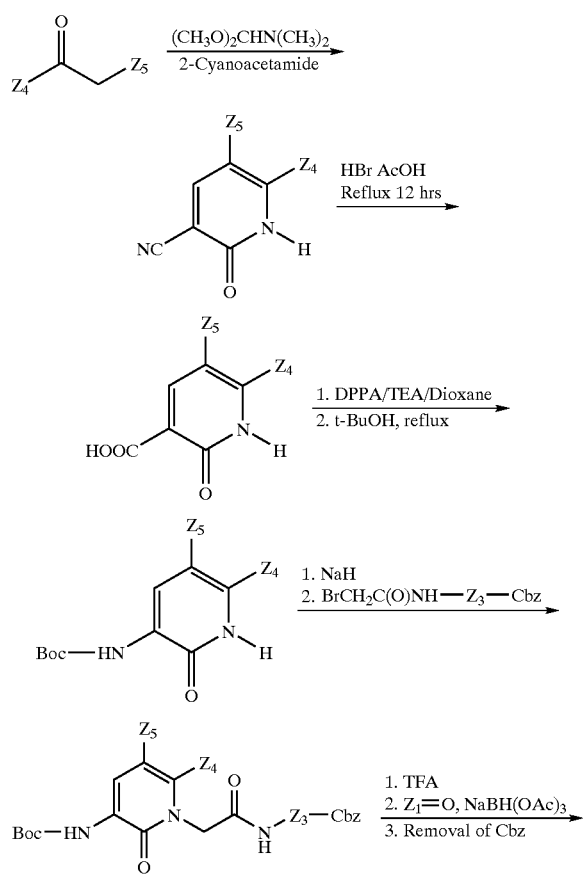
Scheme 4: General Synthesis of Pyridines (I)
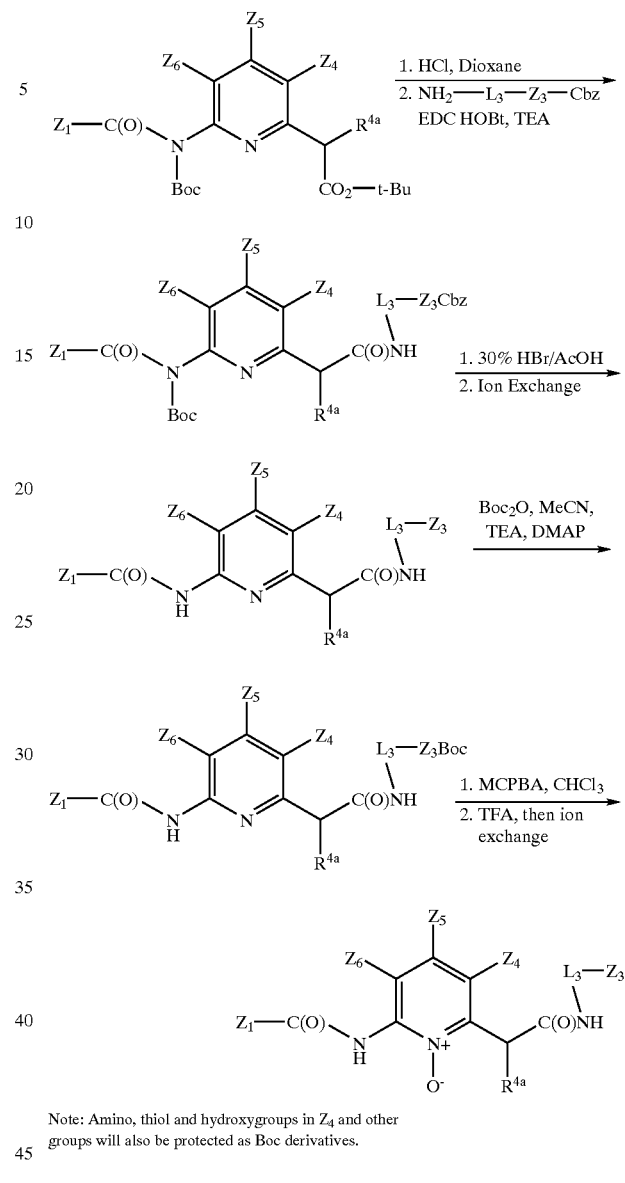
Note: Amino, thiol and hydroxygroups in $Z_4$ and other groups will also be protected as Boc derivatives.
Scheme 5: General Synthesis of Pyridines (II)
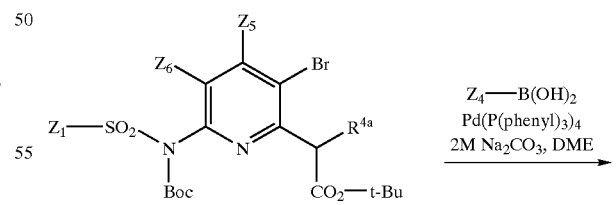
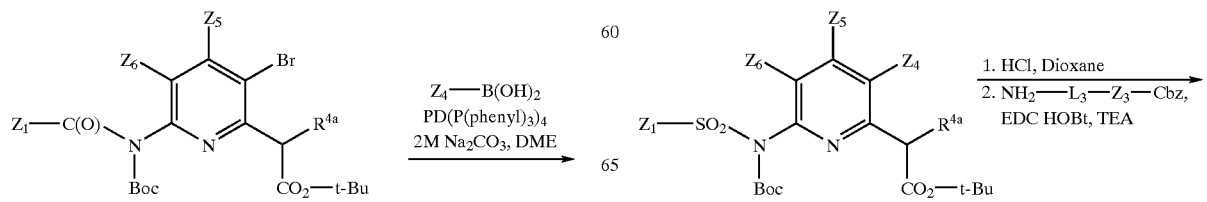

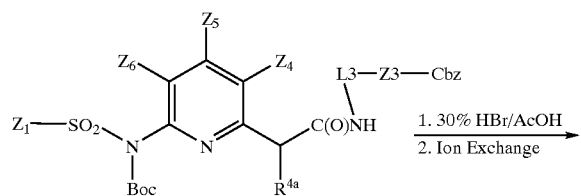
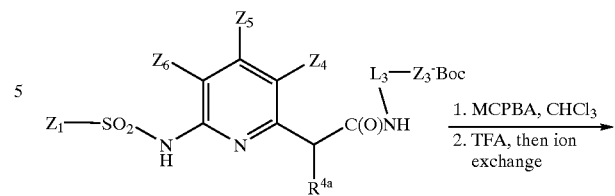
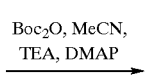
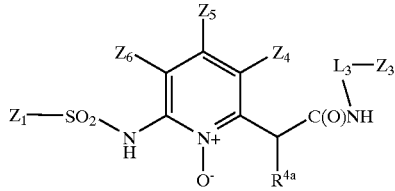
Note: Amino, thiol and hydroxygroups in $Z_4$ and other groups will also be protected as Boc derivatives.
Scheme 6: 4-Piperdinone
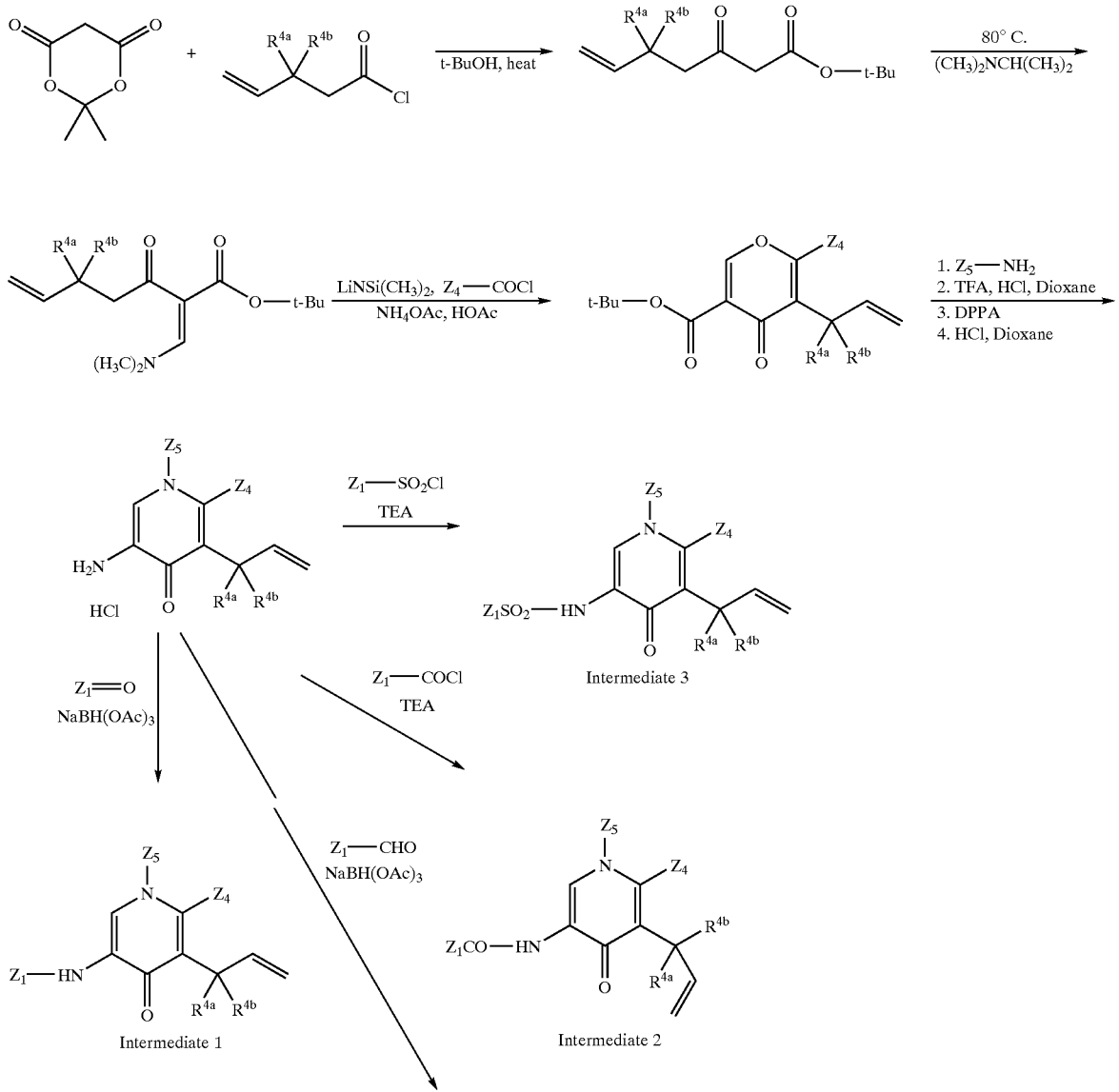

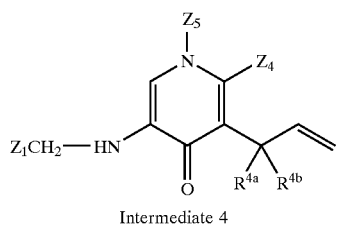
Intermediate 4
Scheme 6: 4-Piperidinone (Intermediate 1)
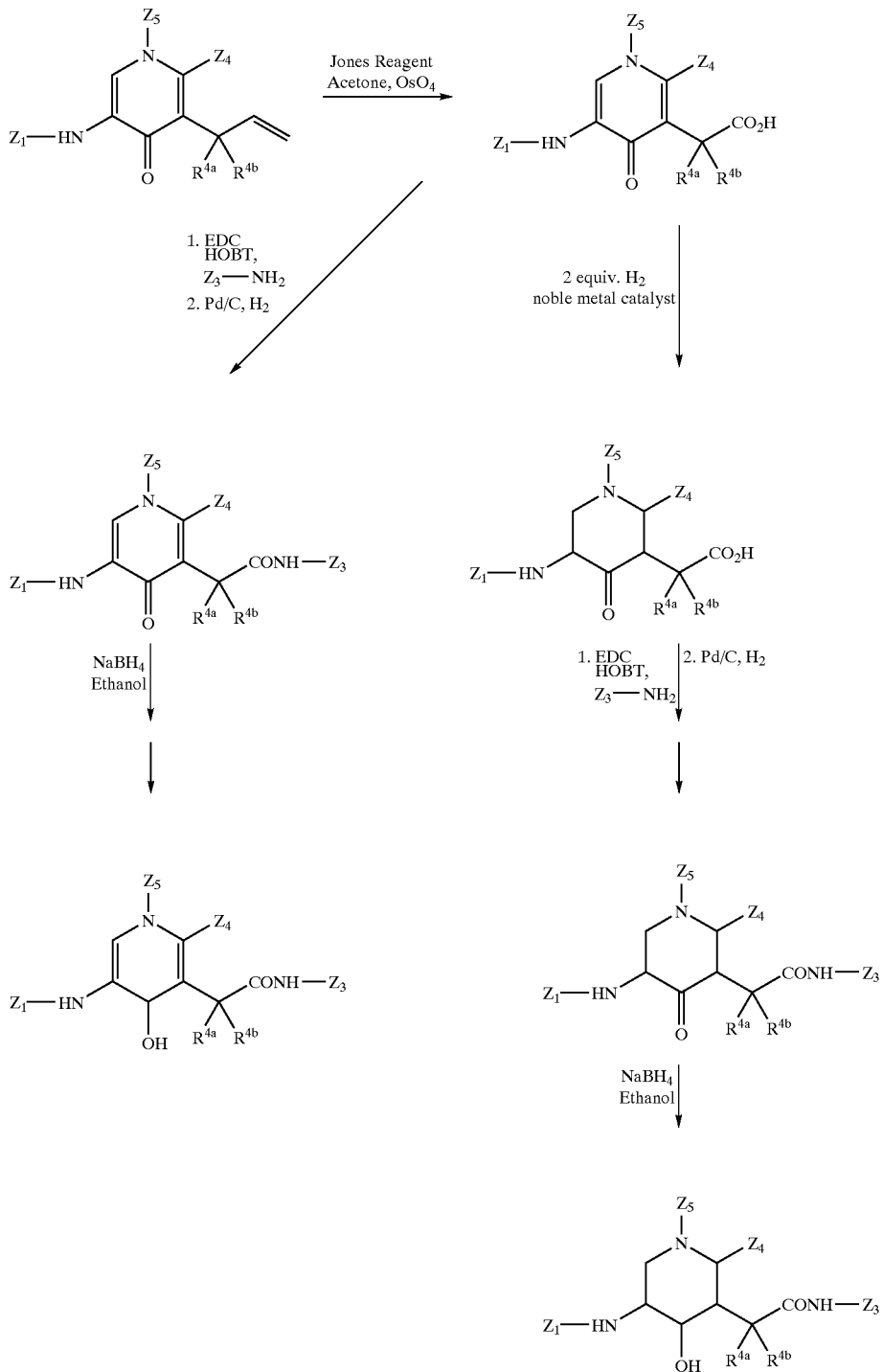

Scheme 6: 4-Piperidinone (Intermediate 2)
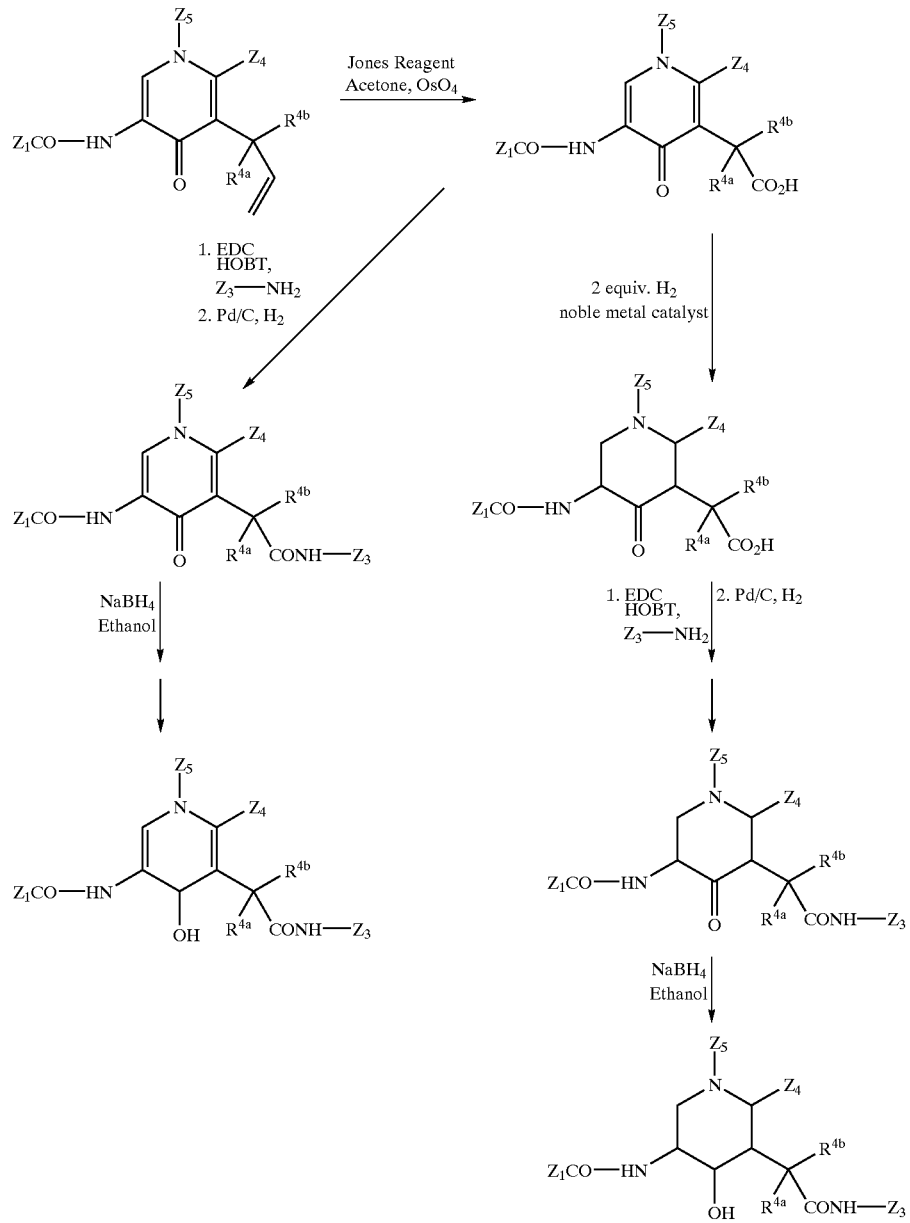
Scheme 6: 4-Piperidinone (Intermediate 3)
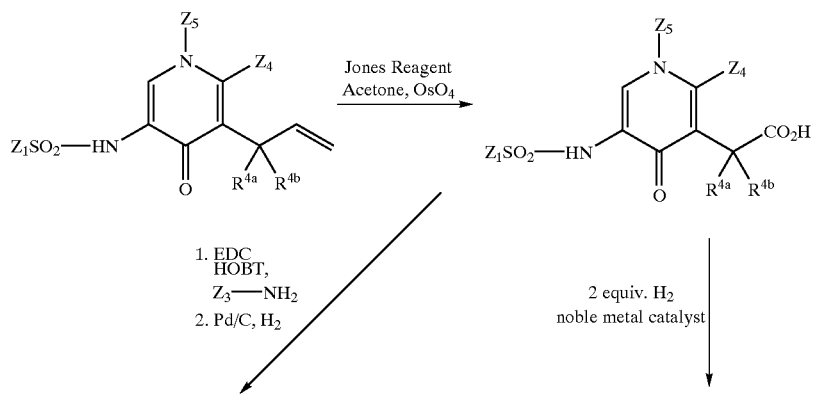

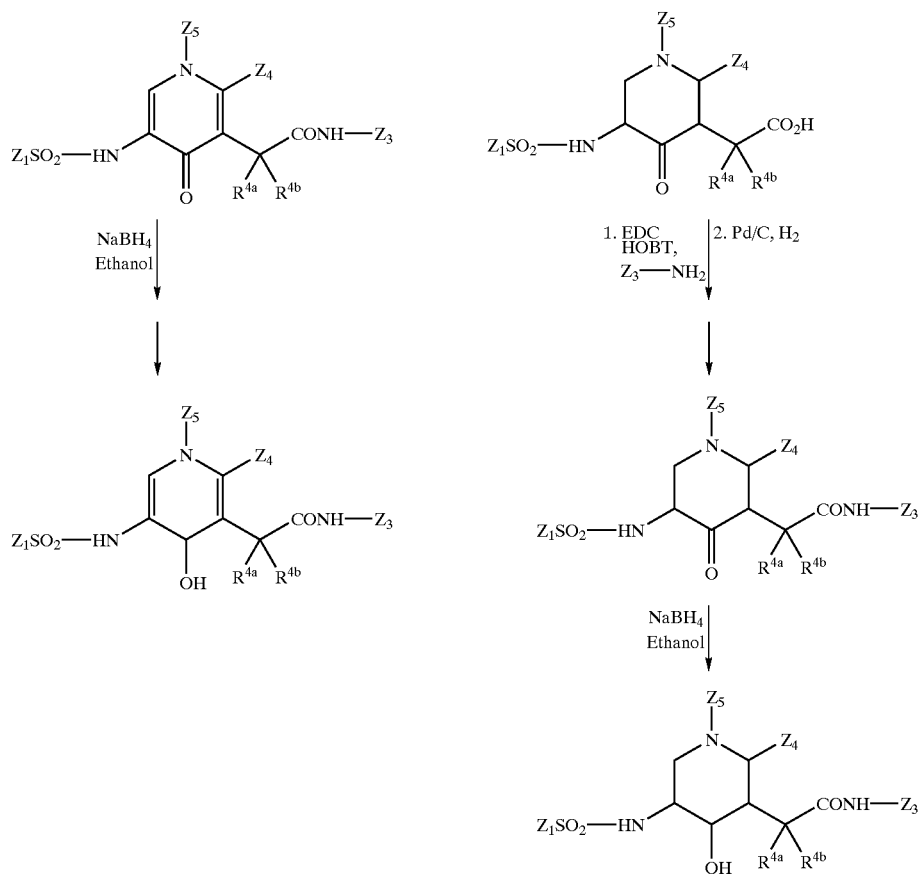
Scheme 6: 4-Piperidinone (Intermediate 4)
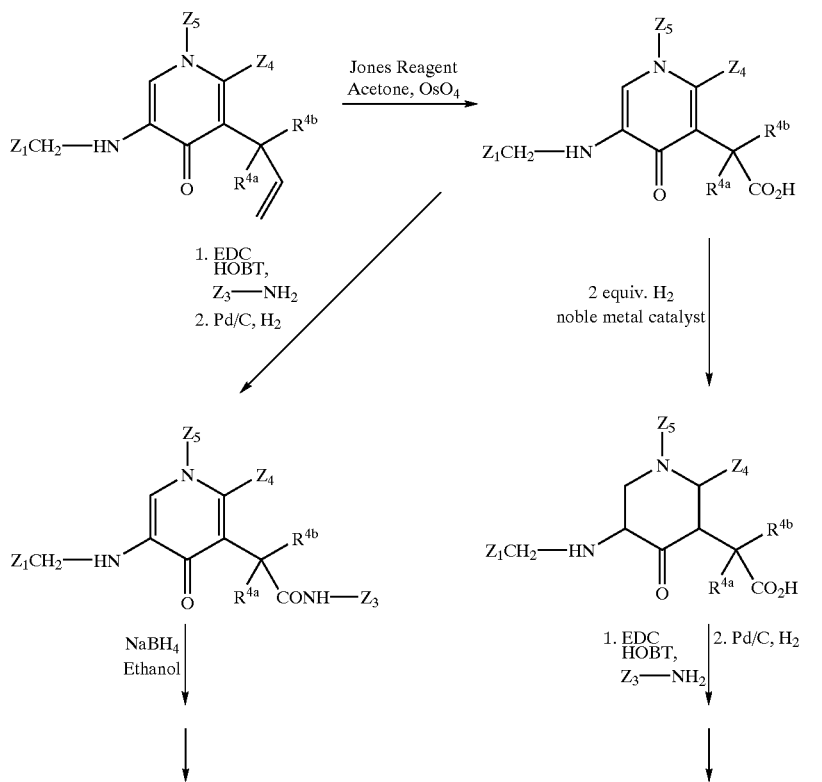

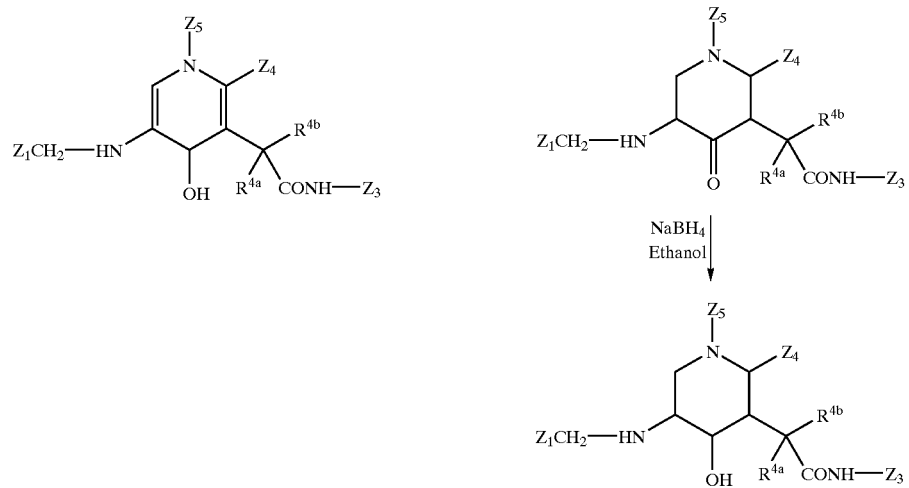
Scheme 7: Cycloalkyl
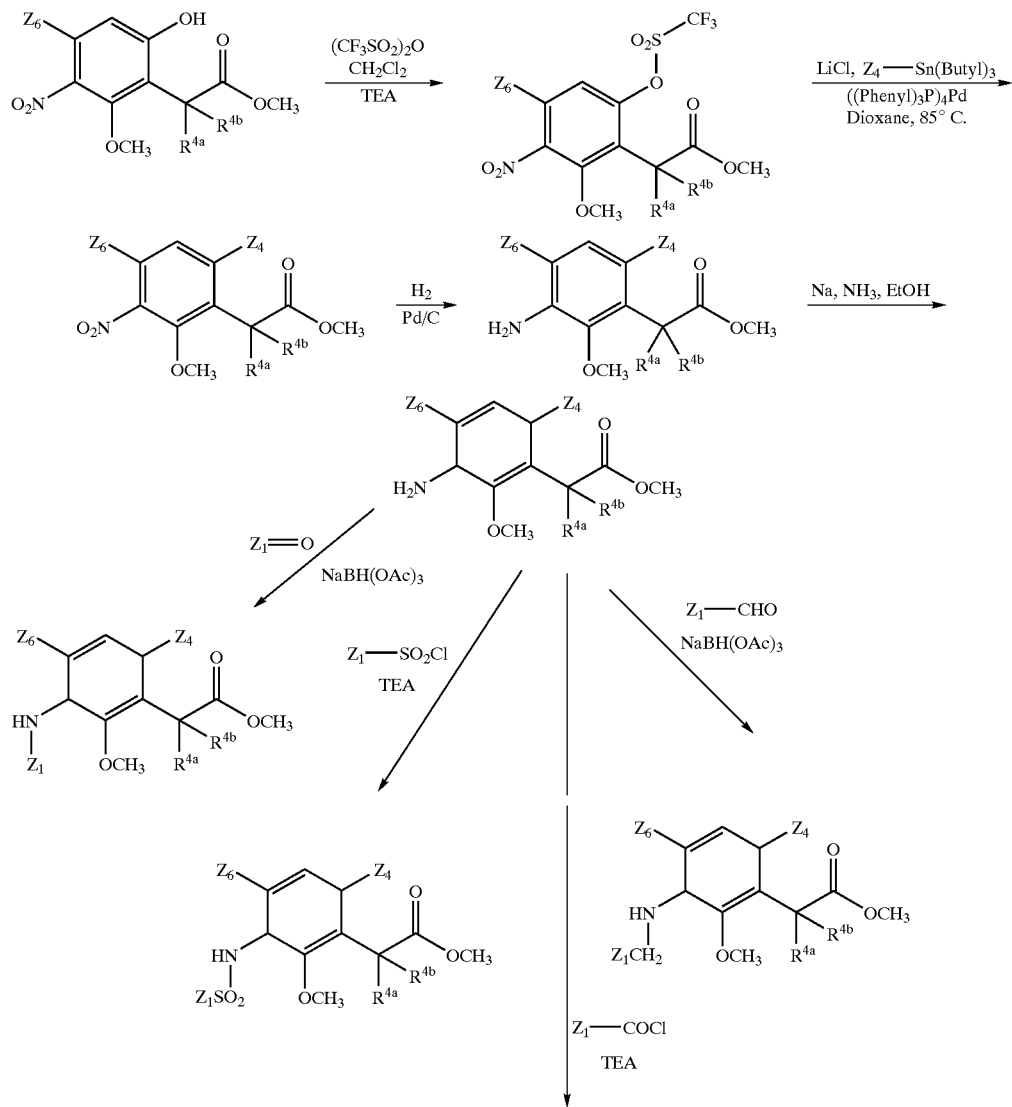

-continued
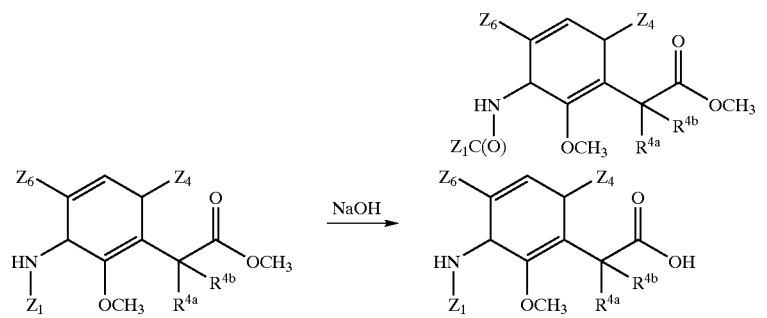
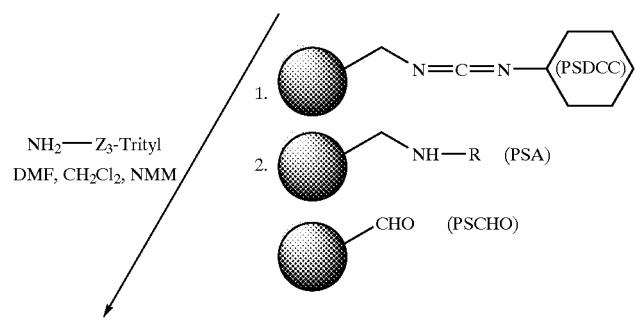
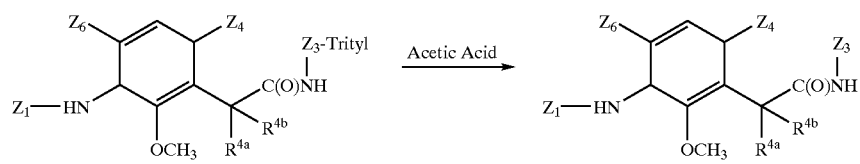
Note: Intermediates derived from the use of $Z_1$—CHO, $Z_1$—$SO_2Cl$, and $Z_1$—COCl can substitute for the one from $Z_1$=O illustrated in this scheme
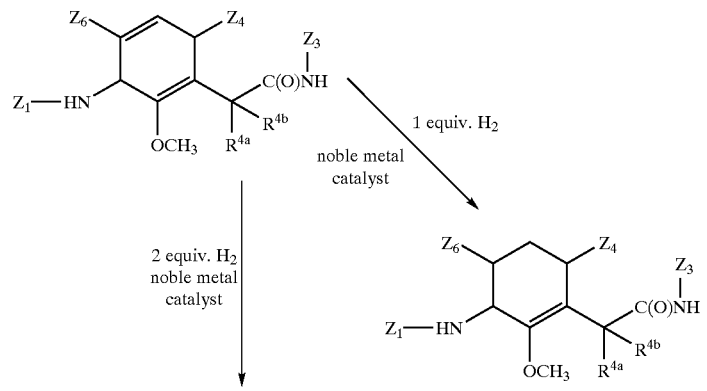
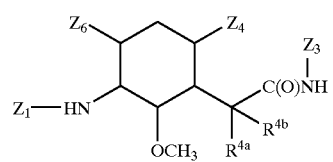

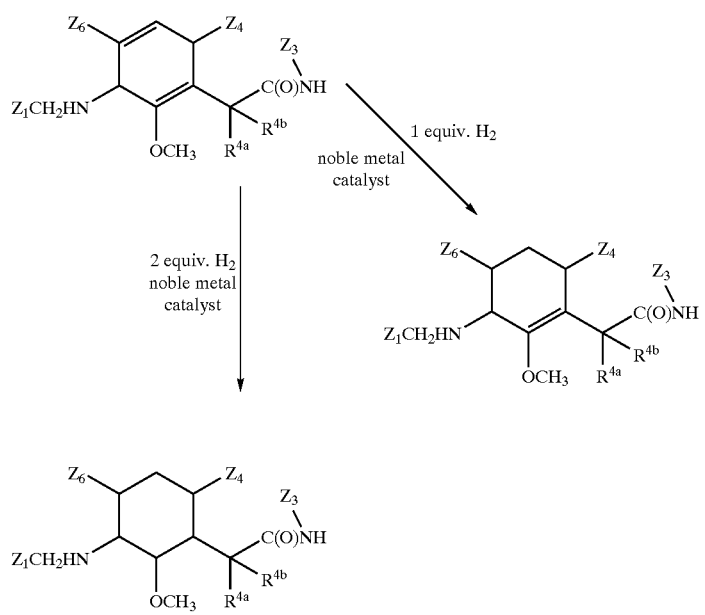
Scheme 8: Reduced Quinone
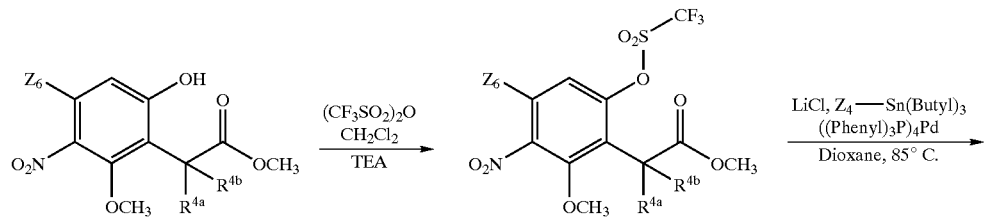
$Z_4$ is selected from the group consisting of aryl (for example, phenyl) and heteroaryl each or which may be optionally substituted.
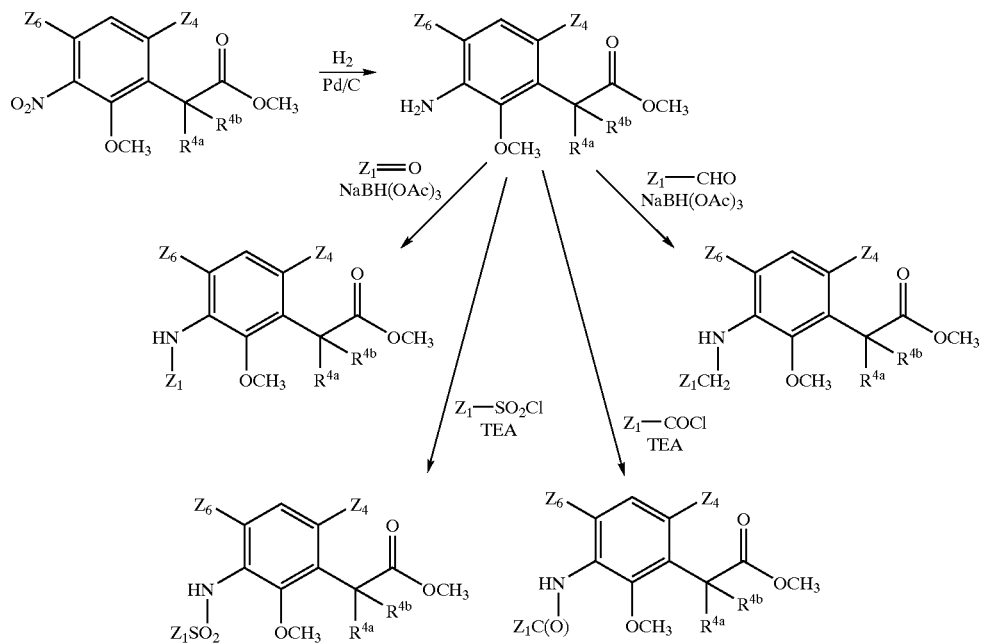

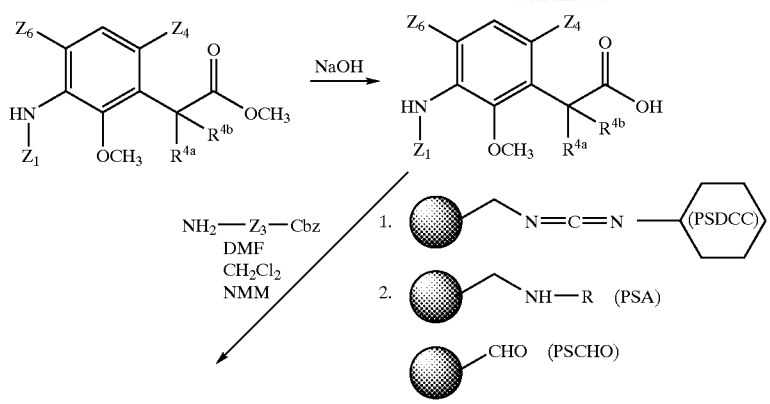
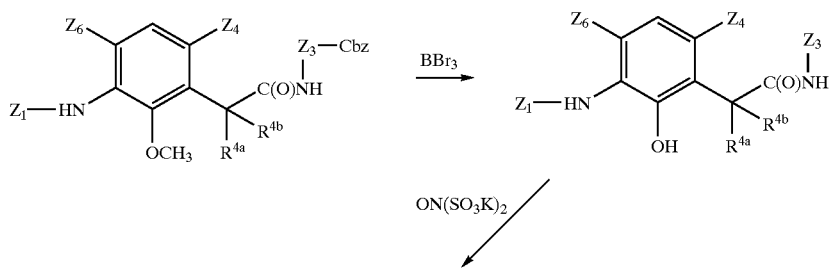
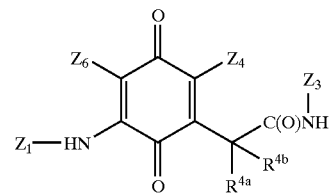
Note: Intermediates derived from the use of $Z_1$—CHO, $Z_1$—$SO_2Cl$, and $Z_1$—COCl can substitute for the one from $Z_1$=O illustrated in this scheme
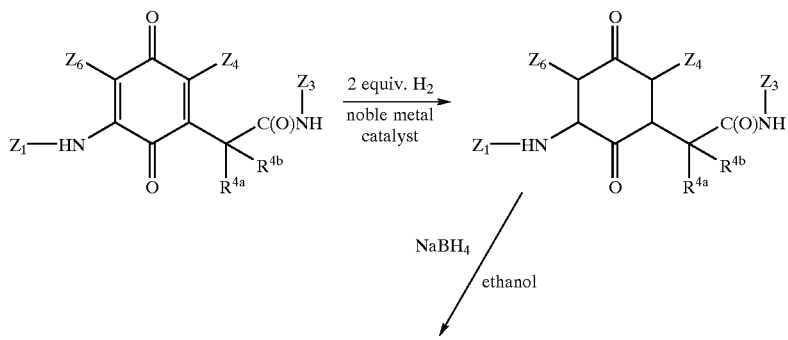
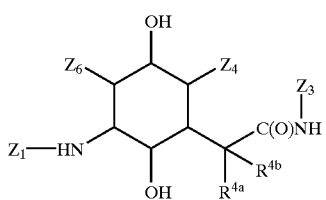

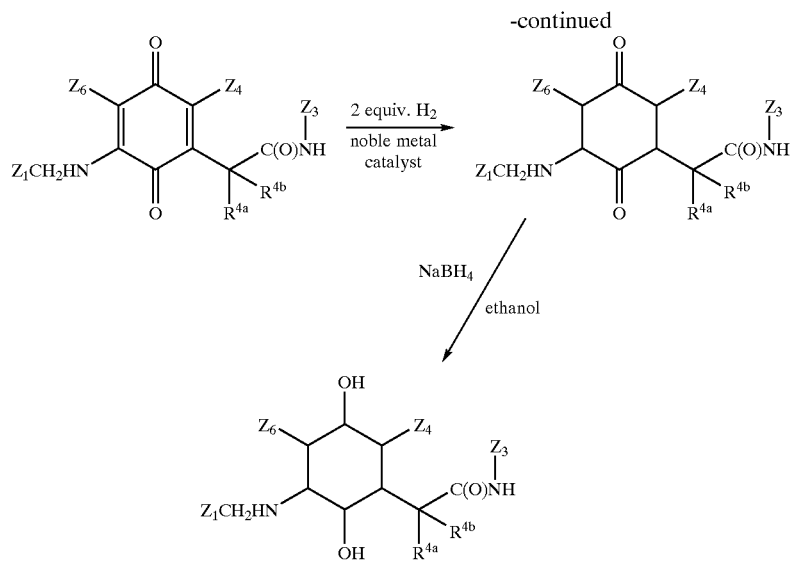
Scheme 9:
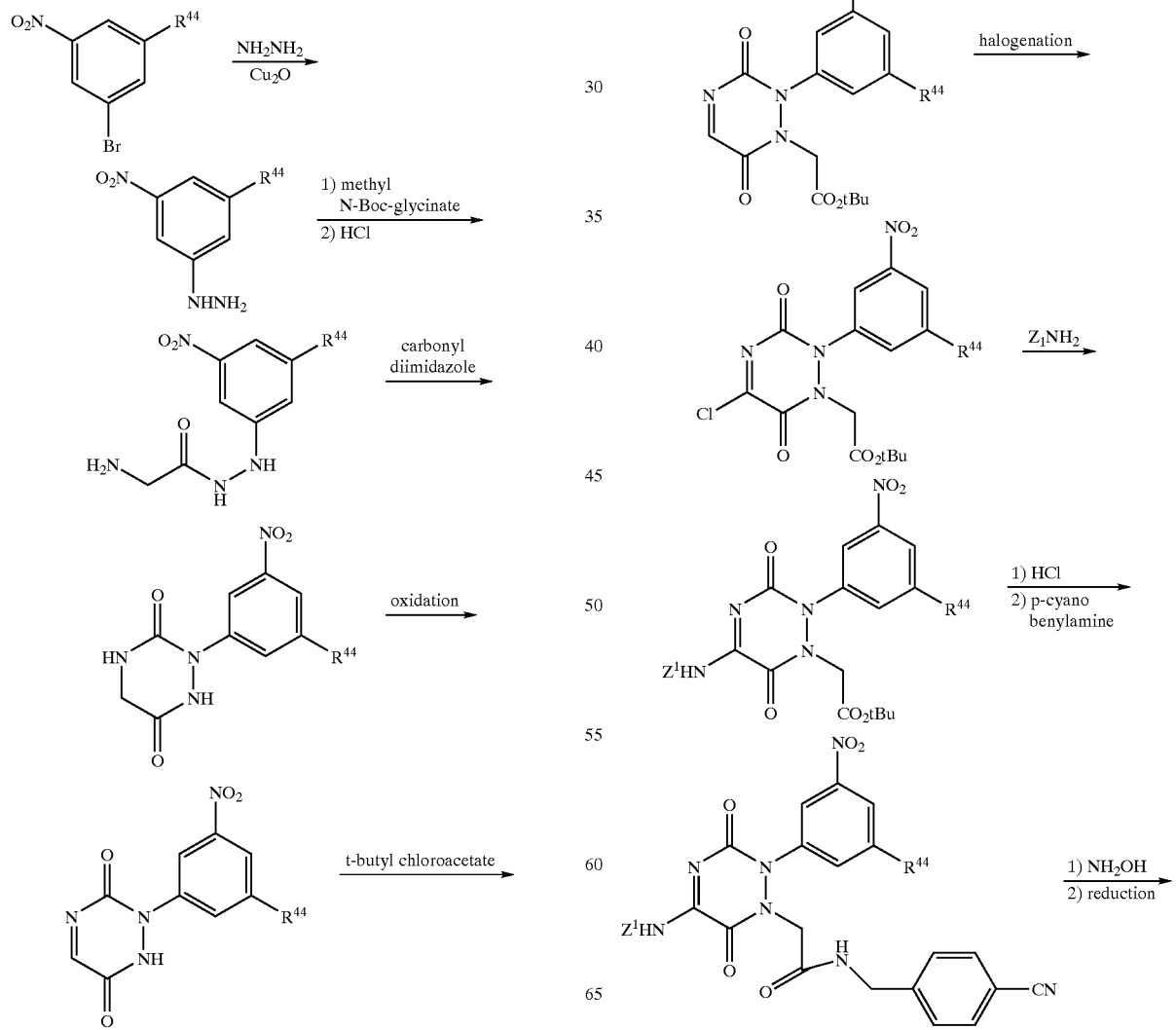

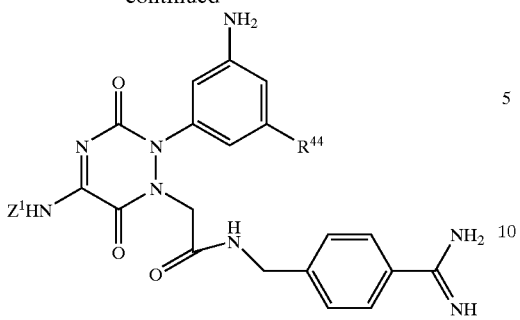

What is claimed is:
1. A compound having the structure:

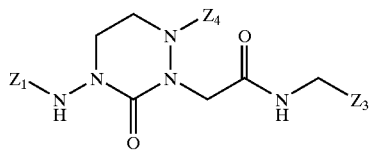

wherein $Z_1$ is selected from the group consisting of an optionally substituted $C_2$ to $C_8$ alkyl, optionally substituted $C_3$ to $C_6$ cycloalkyl and optionally substituted phenyl;

$Z_3$ comprises a 5- or 6-membered heterocyclic or aromatic ring substituted with an amidine or a derivatized amidine group which, upon hydrolysis, oxidation, reduction or elimination yields an amidine group, the ring atoms of the 5- or 6-membered heterocyclic or aromatic ring of $Z_3$ being carbon, sulfur, nitrogen, or oxygen;

$Z_4$ comprises a 5- or 6-membered heterocyclic or carbocyclic ring, the ring atoms of $Z_4$ being $Z_{40}$, $Z_{41}$, $Z_{42}$, $Z_{44}$ and $Z_{45}$, when $Z_4$ is a 5-membered ring and $Z_{40}$, $Z_{41}$, $Z_{42}$, $Z_{43}$, $Z_{44}$ and $Z_{45}$ when $Z_4$ is a 6-membered ring, $Z_{40}$, $Z_{41}$, $Z_{42}$, $Z_{43}$, $Z_{44}$ and $Z_{45}$, being carbon, nitrogen, oxygen or sulfur, $Z_{40}$ being the ring atom through which $Z_4$ is attached to the heterocyclic core ring, $Z_{41}$ and $Z_{45}$ each being in an alpha position relative to $Z_{40}$, $Z_{42}$ and $Z_{44}$ each being in a beta position relative to $Z_{40}$, $Z_{43}$ being in the gamma position relative to $Z_{40}$ when $Z_4$ is a 6-membered ring, $Z_4$ having a substituent $R_{42}$ covalently attached to $Z_{42}$, and a second substituent bonded to one of $Z_{41}$, $Z_{43}$, $Z_{44}$, or $Z_{45}$, the substituent being $R_{41}$ when bonded to $Z_{41}$, the substituent being $R_{43}$ when bonded to $Z_{43}$, the substituent being $R_{44}$ when bonded to $Z_{44}$, and the substituent being $R_{45}$ when bonded to $Z_{45}$;

$R_{42}$ is amino; and $R_{41}$, $R_{43}$, $R_{44}$ and $R_{45}$ are independently hydrogen, hydrocarbyl, substituted hydrocarbyl, heterocyclo, halogen, or a substituted or unsubstituted heteroatom selected from nitrogen, oxygen, sulfur and phosphorus, provided at least one of $R_{41}$, $R_{43}$, $R_{44}$ or $R_{45}$ is other than hydrogen.

2. The compound of claim 1 wherein $Z_1$ is selected from the group consisting of cyclopropyl, isopropyl, methyl, ethyl, cyclobutyl, isobutyl, tert-butyl, sec-butyl, and phenyl optionally substituted at any substitutable position with fluorine, hydroxy, carboxy or alkoxycarbonyl.

3. The compound of claim 2 wherein $Z_1$ is cyclopropyl or isopropyl optionally substituted at any substitutable position with fluorine, hydroxy, carboxy or alkoxycarbonyl.

4. The compound of claim 1 wherein $Z_3$ comprises a substituted phenyl, thienyl, or furanyl ring, the phenyl, thienyl or furanyl ring being substituted with an amidine or a derivatized amidine group, and optionally further substituted at any substitutable position with fluorine, hydroxy, carboxy, alkoxycarbonyl, or hydrocarbyloxy.

5. The compound of claim 4 wherein $Z_3$ is

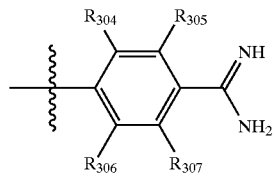

wherein
$R_{304}$ and $R_{306}$ are independently selected from the group consisting of hydrogen, fluorine, hydroxy, carboxy, hydrocarbyloxy and alkoxycarbonyl; and
$R_{305}$ and $R_{307}$ are independently selected from the group consisting of hydrogen, fluorine, methoxy, hydroxy and carboxy.

6. The compound of claim 4 wherein the 5- or 6-membered heterocyclic or aromatic ring comprising $Z_3$ is substituted with a derivatized amidine which, upon hydrolysis, oxidation, reduction or elimination, or any combination thereof, yields an amidine group.

7. The compound of claim 1 wherein $Z_4$ has the following structure:

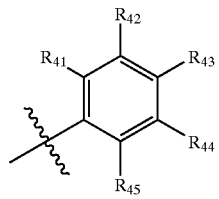

wherein
$R_{42}$ is amino;
$R_{44}$ is hydrocarbyl, substituted hydrocarbyl, halogen or an optionally substituted heteroatom selected from the group consisting of oxygen, nitrogen, and sulfur; and
$R_{41}$, $R_{43}$ and $R_{45}$ are independently hydrogen, hydrocarbyl, substituted hydrocarbyl, halogen or an optionally substituted heteroatom selected from the group consisting of oxygen, nitrogen, and sulfur.

8. The compound of claim 7 wherein $R_{41}$, $R_{43}$ and $R_{45}$ are independently hydrogen, halogen, alkoxy, or alkyl, optionally substituted with halogen or alkoxy and $R_{42}$ and $R_{44}$ are as defined in claim 7.

9. The compound of claim 7 wherein $R_{44}$ is selected from the group consisting of hydroxy, carboxy, carboxamido, alkoxy, alkylsulfonyl, sulfonamido, or alkoxycarbonyl.

10. The compound of claim 9 wherein $R_{44}$ is sec-butylamide, carboxy, ethoxycarbonyl, isopropoxycarbonyl, butoxycarbonyl, isopropylamide or hydroxy.

11. The compound of claim 1 wherein $Z_4$ has the following structure:

wherein $Z_{40}$, $Z_{41}$, $Z_{42}$, $Z_{44}$, and $Z_{45}$ are independently selected from the group consisting of carbon, nitrogen, oxygen and sulfur;

$R_{42}$ is amino;

$R_{44}$ is hydrocarbyl, substituted hydrocarbyl, halogen or an optionally substituted heteroatom selected from the group consisting of oxygen, nitrogen, and sulfur; and $R_{41}$ and $R_{45}$ are independently hydrogen, hydrocarbyl, substituted hydrocarbyl, halogen or an optionally substituted heteroatom selected from the group consisting of oxygen, nitrogen, and sulfur.

12. The compound of claim 11 wherein $R_{41}$ and $R_{45}$ are independently hydrogen, halogen, alkoxy, or alkyl, optionally substituted with halogen or alkoxy and $R_{42}$ and $R_{44}$ are as defined in claim 11.

13. The compound of claim 11 wherein $R_{44}$ is selected from the group consisting of hydroxy, carboxy, carboxamido, alkoxy, alkylsulfonyl, sulfonamido, or alkoxycarbonyl.

14. The compound of claim 13 wherein $R_{44}$ is sec-butylamide, carboxy, ethoxycarbonyl, isopropoxycarbonyl, butoxycarbonyl, isopropylamide or hydroxy.

* * * * *